(12) United States Patent
Chen

(10) Patent No.: US 11,058,708 B2
(45) Date of Patent: Jul. 13, 2021

(54) RNA INTERFERENCE OF GALECTIN-3 EXPRESSION AND METHODS OF USE THEREOF

(75) Inventor: Swey-Shen Chen, San Diego, CA (US)

(73) Assignee: Sweyshen Chen, San Diego (CA)

( * ) Notice: Subject to any disclaimer, the term of this patent is extended or adjusted under 35 U.S.C. 154(b) by 0 days.

(21) Appl. No.: 13/156,350

(22) Filed: Sep. 19, 2011

(65) Prior Publication Data

US 2013/0072540 A1    Mar. 21, 2013

(51) Int. Cl.
*C12N 15/11* (2006.01)
*A61K 31/713* (2006.01)
*C12N 15/113* (2010.01)

(52) U.S. Cl.
CPC ........ *A61K 31/713* (2013.01); *C12N 15/1138* (2013.01); *C12N 2310/14* (2013.01); *C12N 2310/531* (2013.01); *C12N 2799/027* (2013.01)

(58) Field of Classification Search
CPC .......... C12N 15/1138; C12N 2310/531; C12N 2310/14
See application file for complete search history.

(56) References Cited

U.S. PATENT DOCUMENTS

| 2005/0207974 A1* | 9/2005 | Deng | A61K 47/6425 |
| | | | 424/1.49 |
| 2007/0031844 A1* | 2/2007 | Khvorova et al. | 435/6 |
| 2008/0113351 A1* | 5/2008 | Naito | A61K 31/713 |
| | | | 435/6.11 |

FOREIGN PATENT DOCUMENTS

WO    WO-2009001359 A2 * 12/2008 ............... A61P 9/10

OTHER PUBLICATIONS

Watts, et al. (2008) "Chemically modified siRNA: tools and applications." Drug Discovery Today, vol. 13(19/20):842-855. (Year: 2008).*

* cited by examiner

*Primary Examiner* — Ekaterina Poliakova-Georgantas

(57) ABSTRACT

Galectin-3 is a pro-inflammatory molecule functioning as a cytokine hub, and also regulates unfolded protein responses (UPR) and ER stress. Thus, galectin-3 serves as a target for ameliorating inflammatory diseases such as allergic inflammation and diabetic inflammation and insulin resistance. RNA interference of endogenous galectin-3 expression, upregulates IL-12, IL-10 while downregulating IL-23 production, which offers protection against allergic inflammation. In addition, endogenous galectin-3 knockdown causes upregulation of XBP1, alleviating ER stress. Together, upregulated XBP1 and IL-10 offer protection against obesity-induced inflammation. Therefore, the embodiment of the invention resides in RNA interference of endogenous galectin-3 in appropriate cell types in order to rectify allergic and/or diabetic inflammation.

3 Claims, 21 Drawing Sheets

Figure 6:
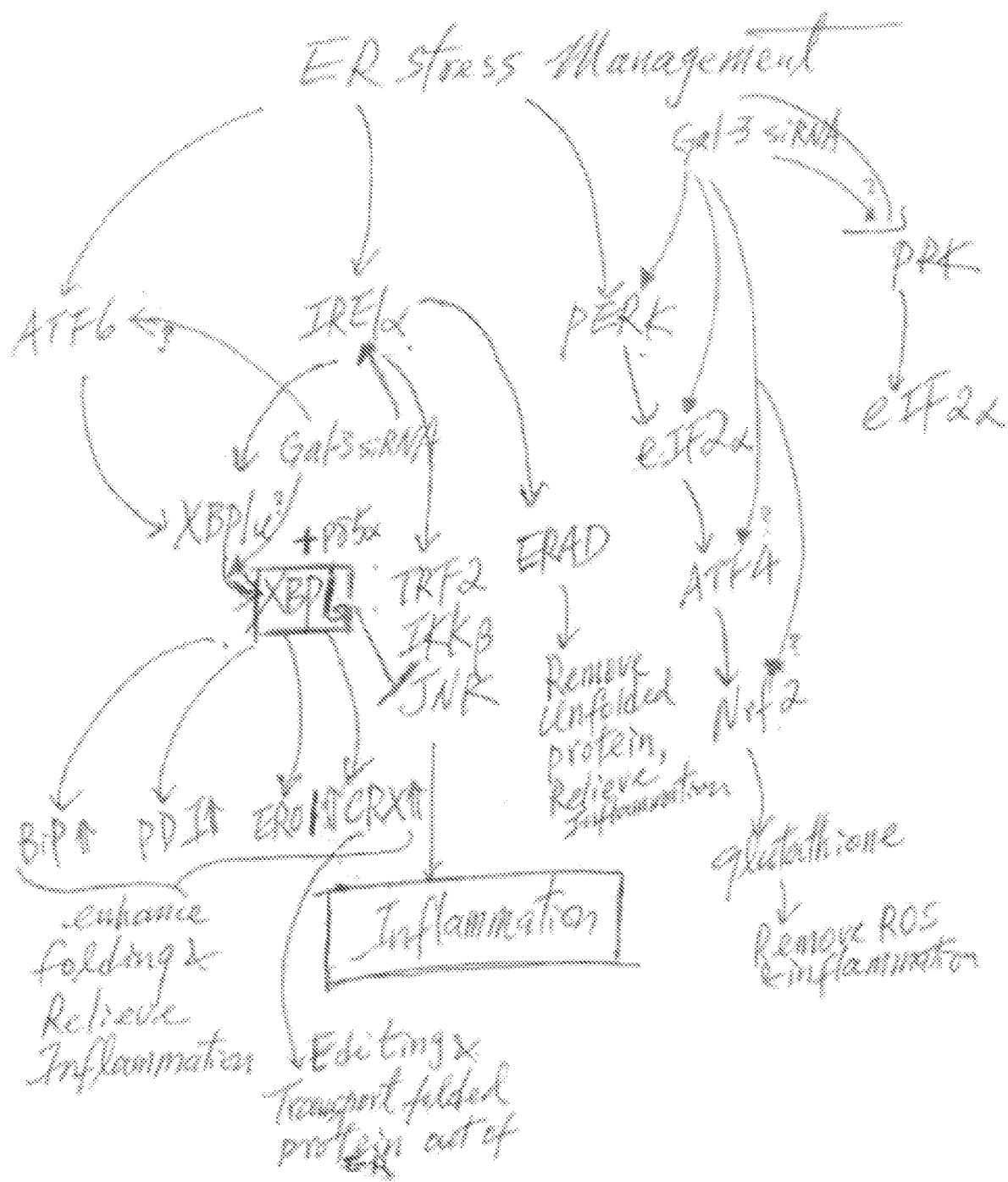

Specification includes a Sequence Listing.

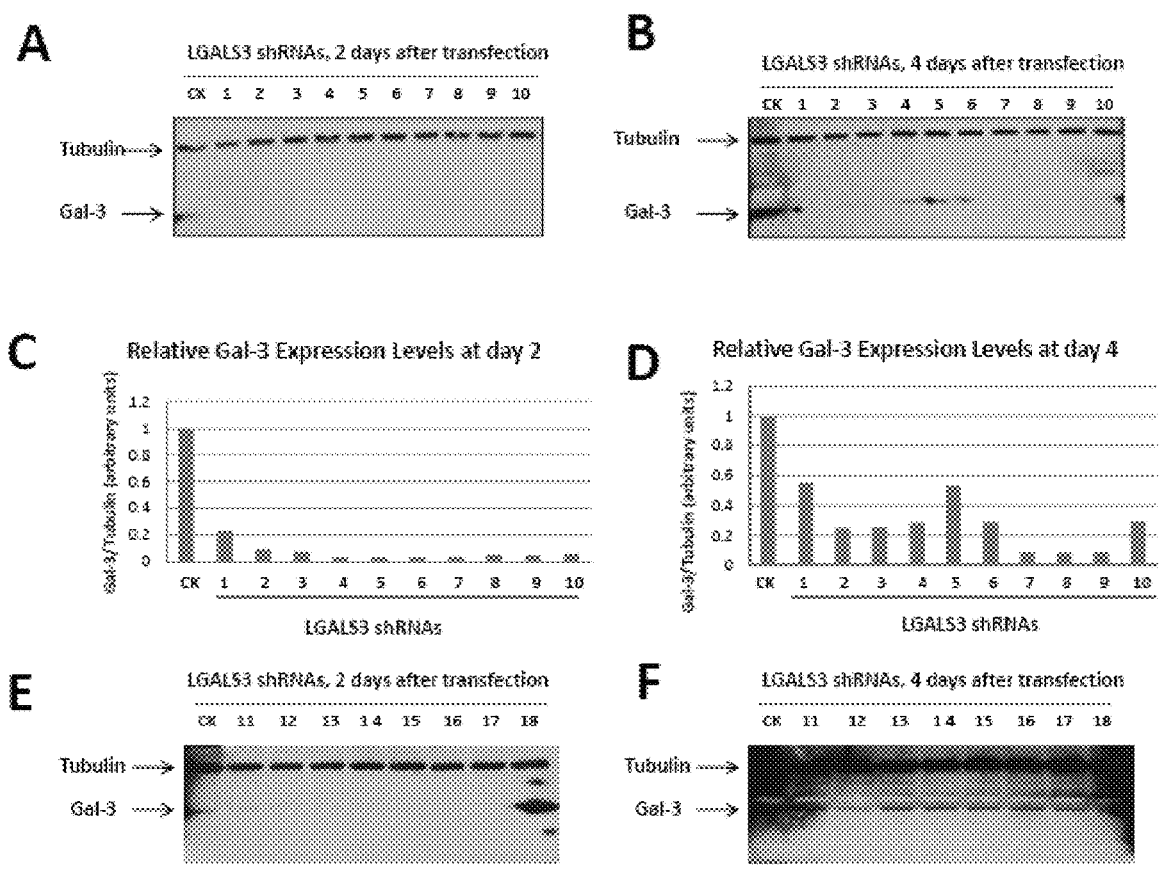

Figure 2. Short hairpin RNAs (shRNAs) down-regulated galectin-3 transcripts.
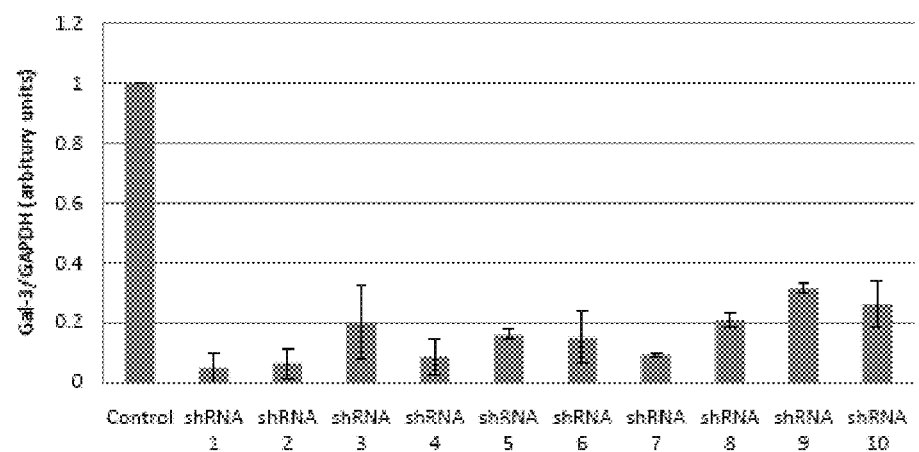
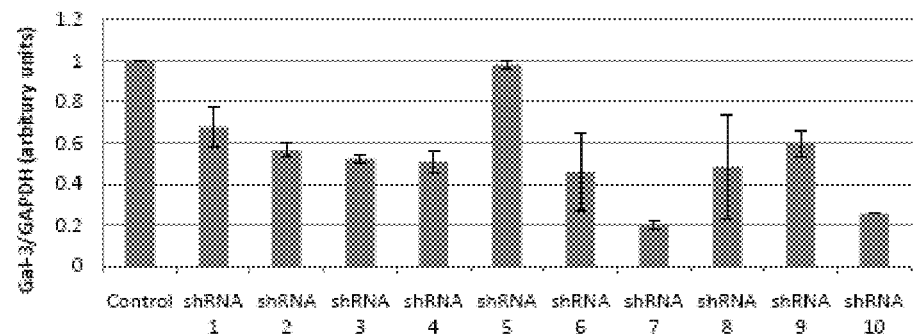

Figure 3. Upregulation of XBP1 downstream folding proteins in galectin-3 knockdown HEK293 cells
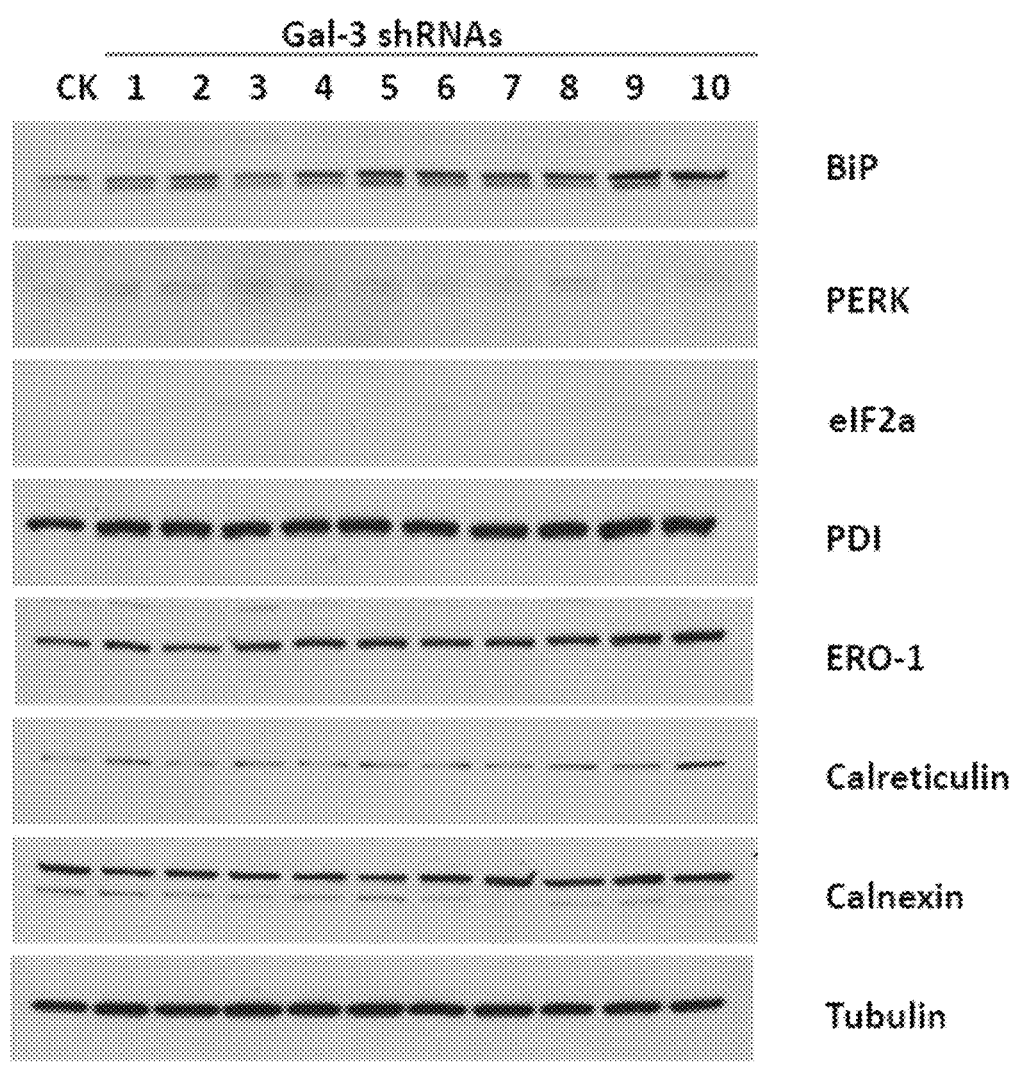

Figure 4. Upregulation of spliced XBP1 message in galectin-3 knockdown HEK293 cells
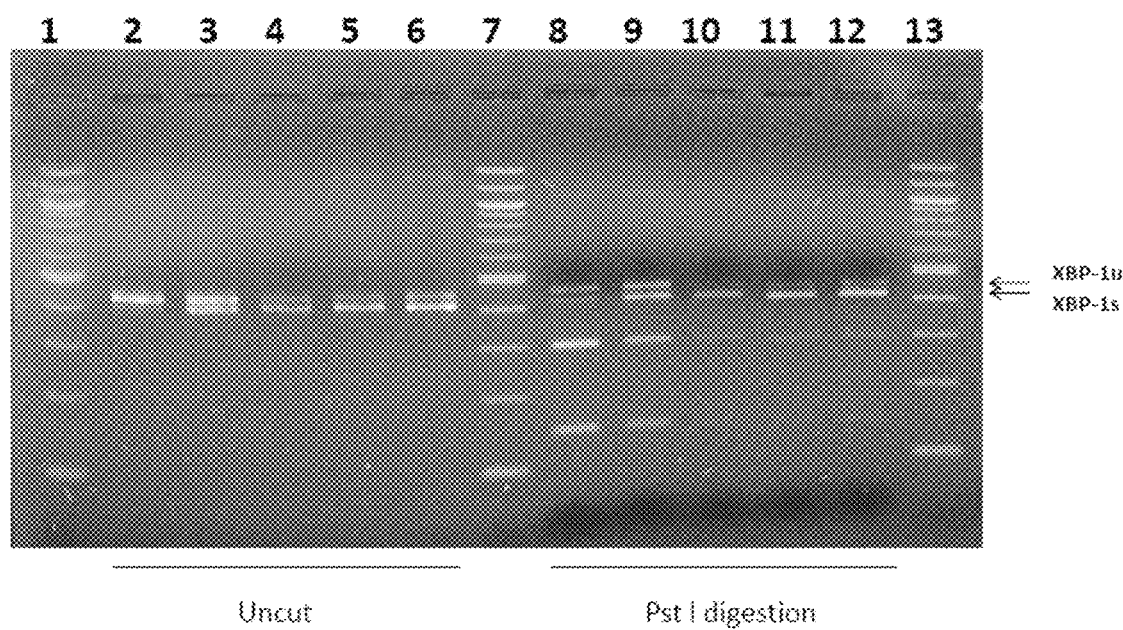

Figure 5. Upregulation of mature XBP1 protein in galectin-3 knockdown HEK293 cells
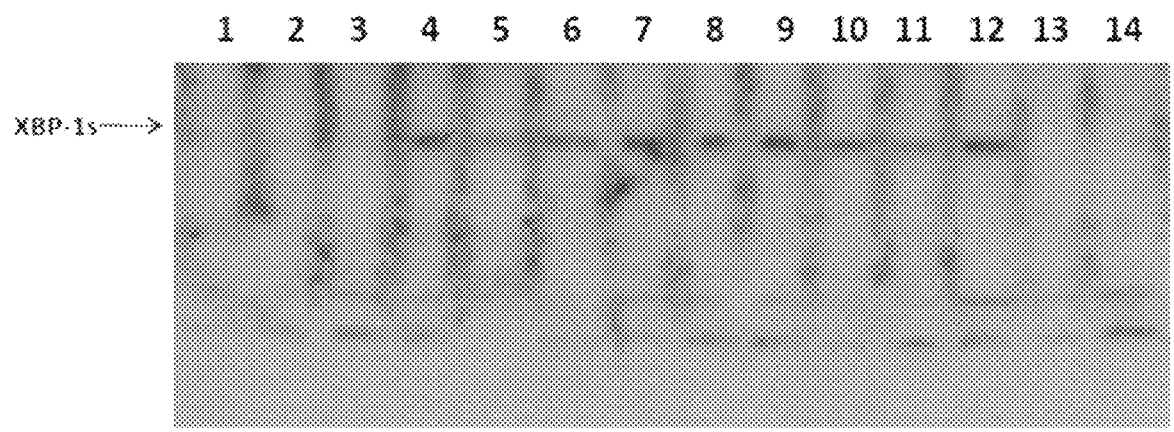

Figure 7A. Galectin-3 siRNA inhibits galectin-3 protein expression in human MoDCs
A
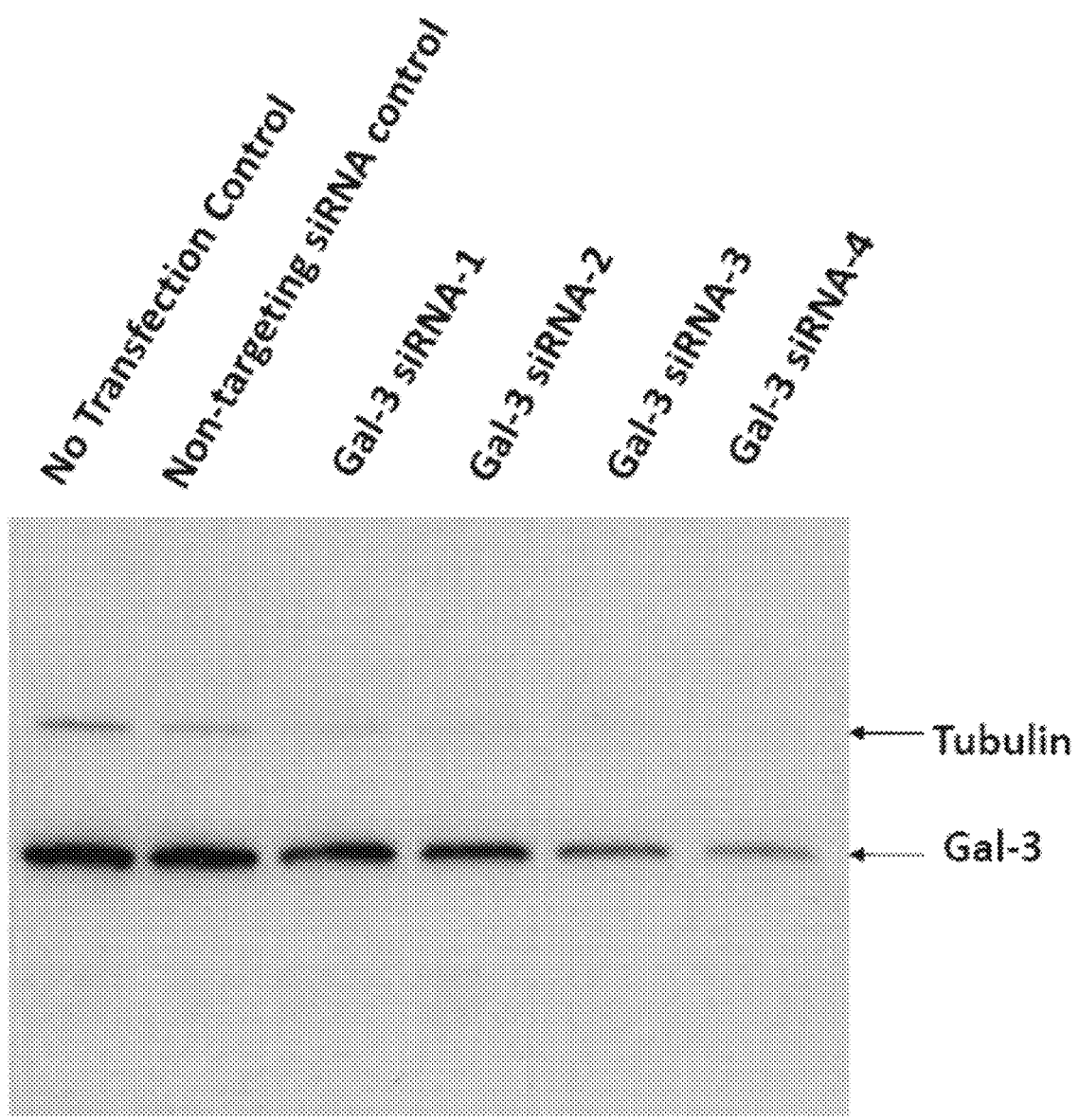

Figure 7B. Galectin-3 siRNA inhibits galectin-3 protein expression in RAW264.7 macrophages
B
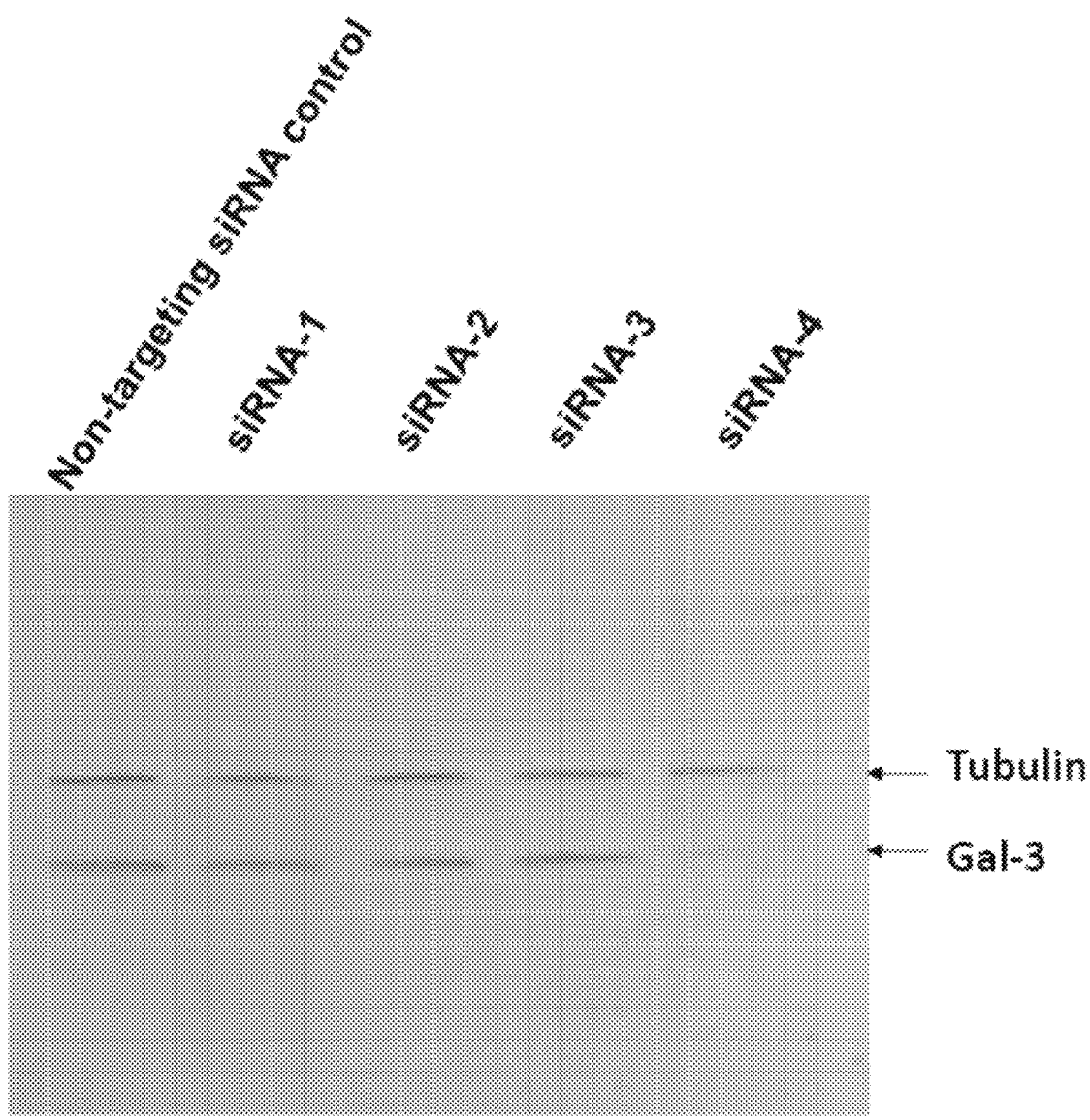

Figure 8A/B. Expression of IL-12 in human MoDCs.
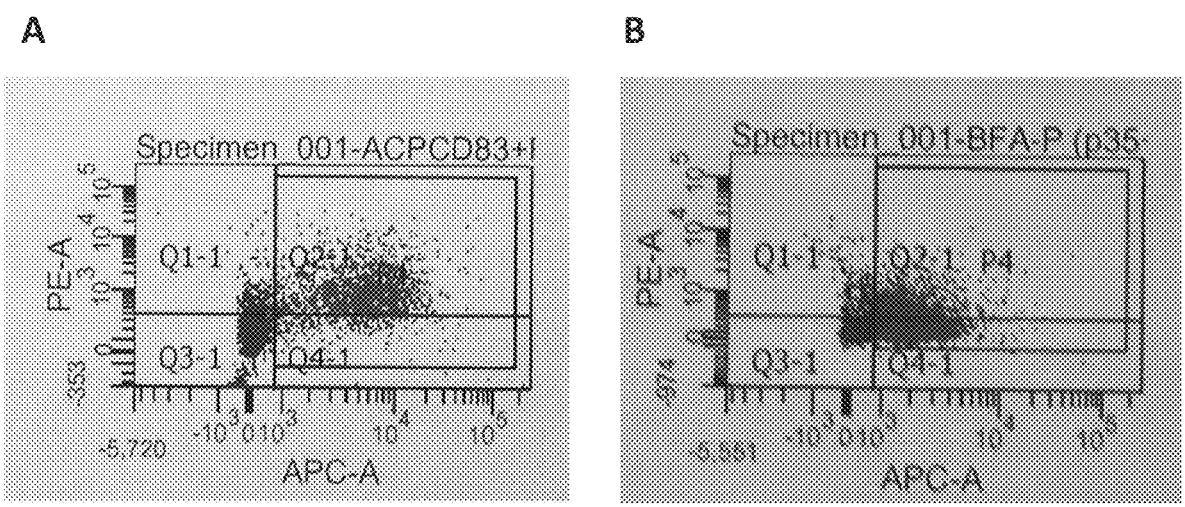

Figure 8C. Galectin-3 siRNA inhibits galectin-3 protein expression in human MoDCs
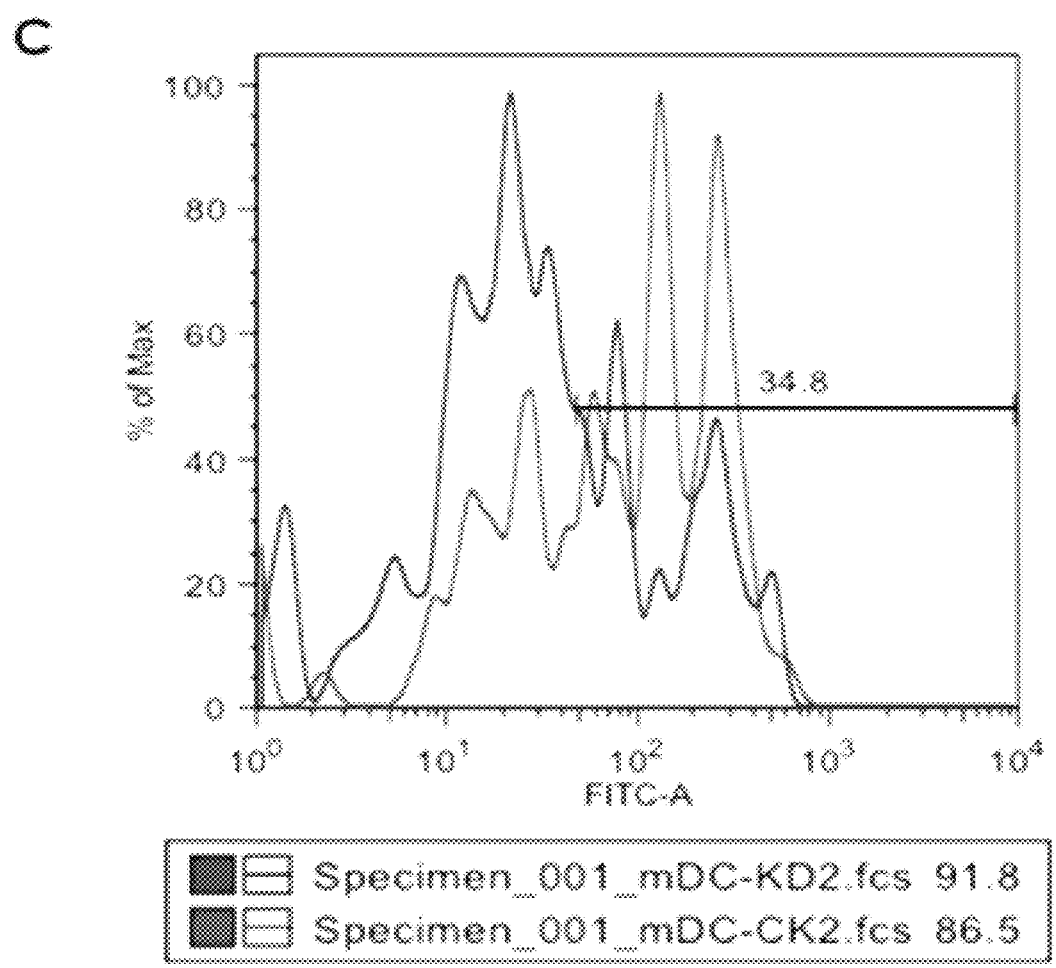

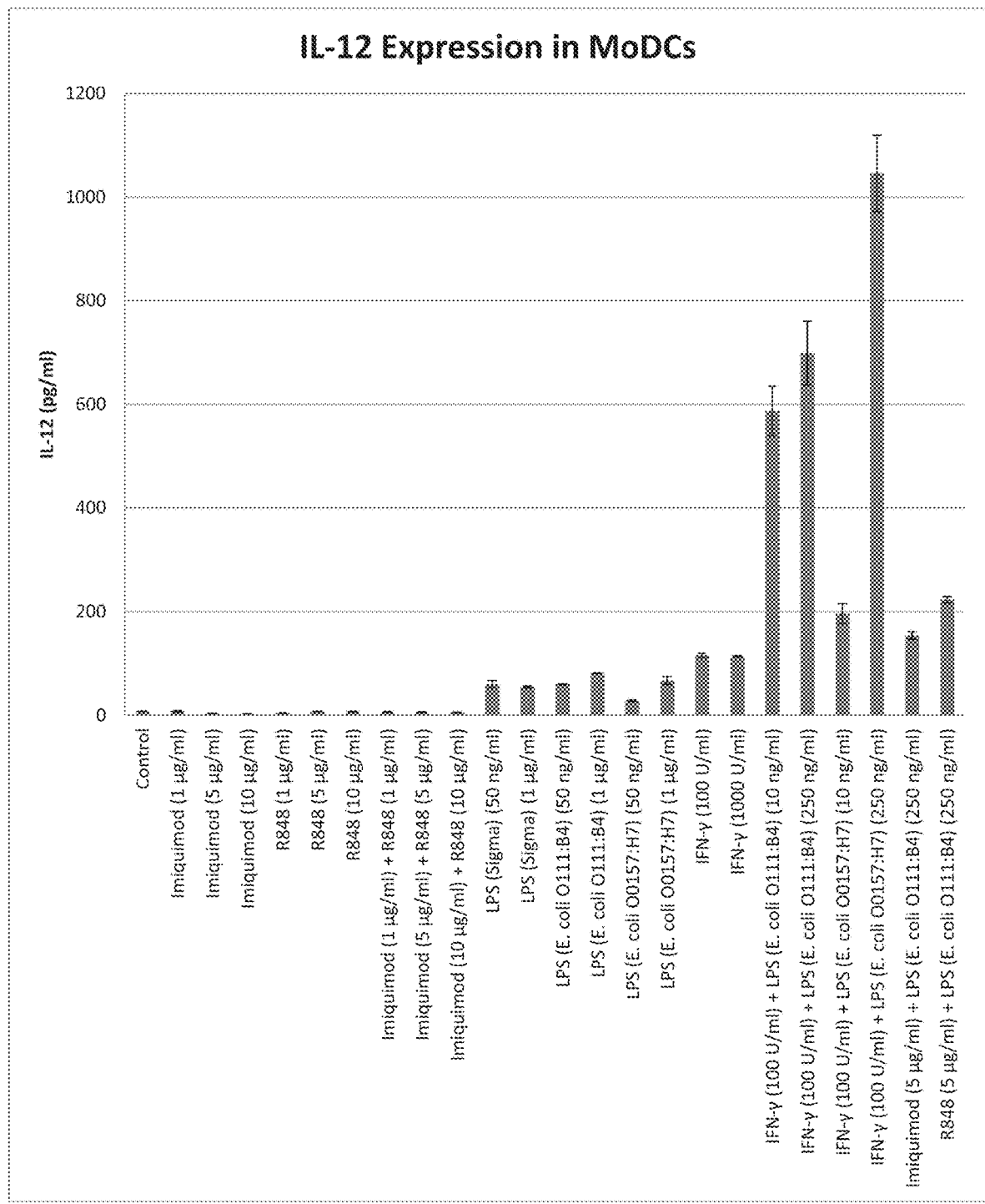
Figure 9A. IL-12 production by MoDCs stimulated by innate TLR ligands Figure 9B. IL-23 production by MoDC stimulated by innate TLR ligands
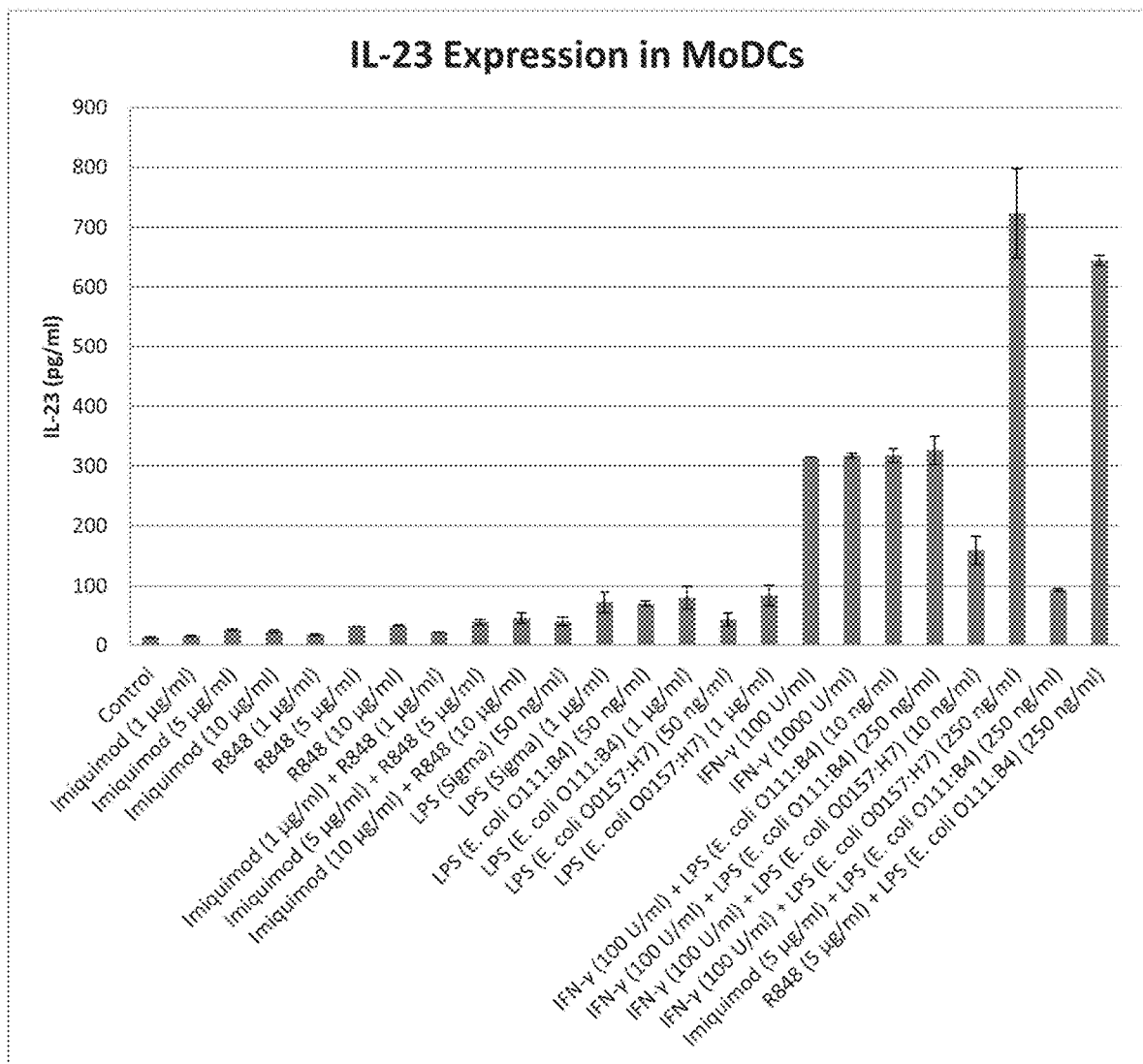

Figure 9C. Galectin-3 knockdown abrogates galectin-3 mRNA expression in MoDCs stimulated with innate TLR ligands
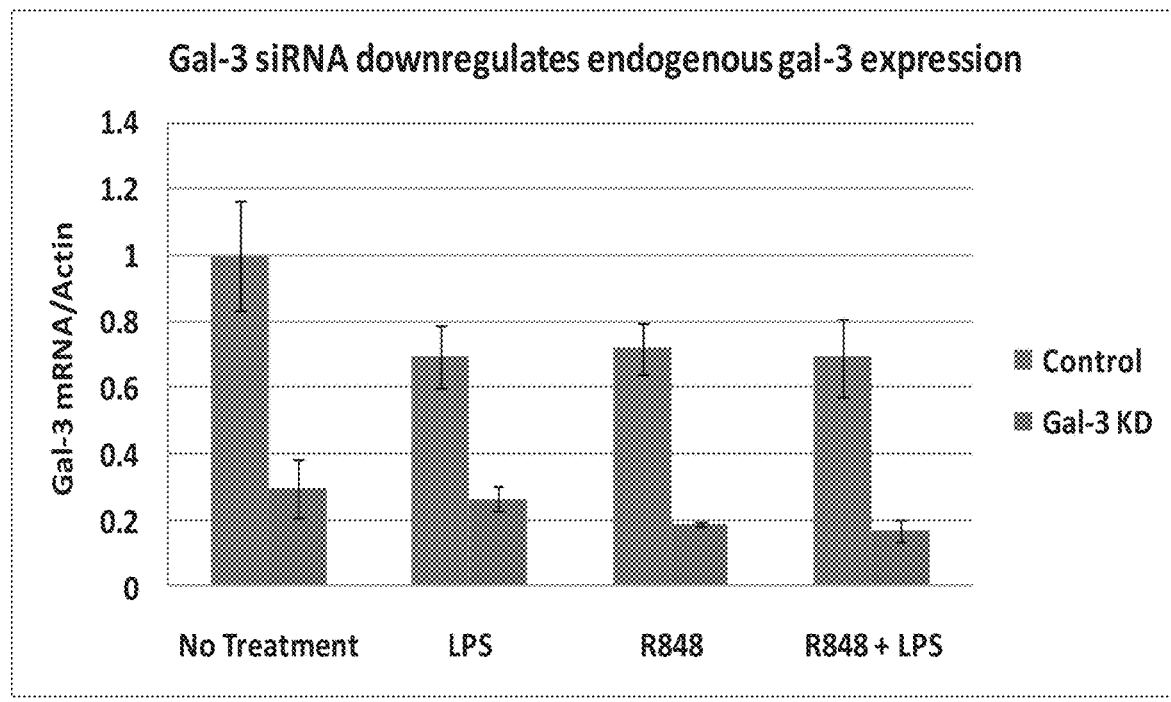

Figure 10. Diagram of galectin-3 as the molecular hub for controlling cytokine responses in dendritic cells and macrophages in allergic inflammation
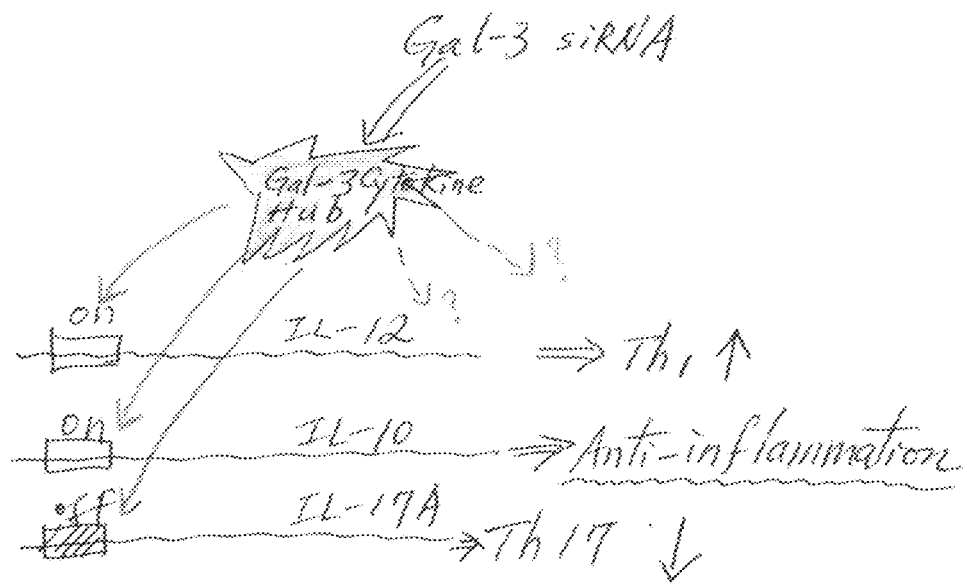

Figure 11A. Galectin-3 knockdown upregulates IL-12 production in TLR-stimulated MoDCs
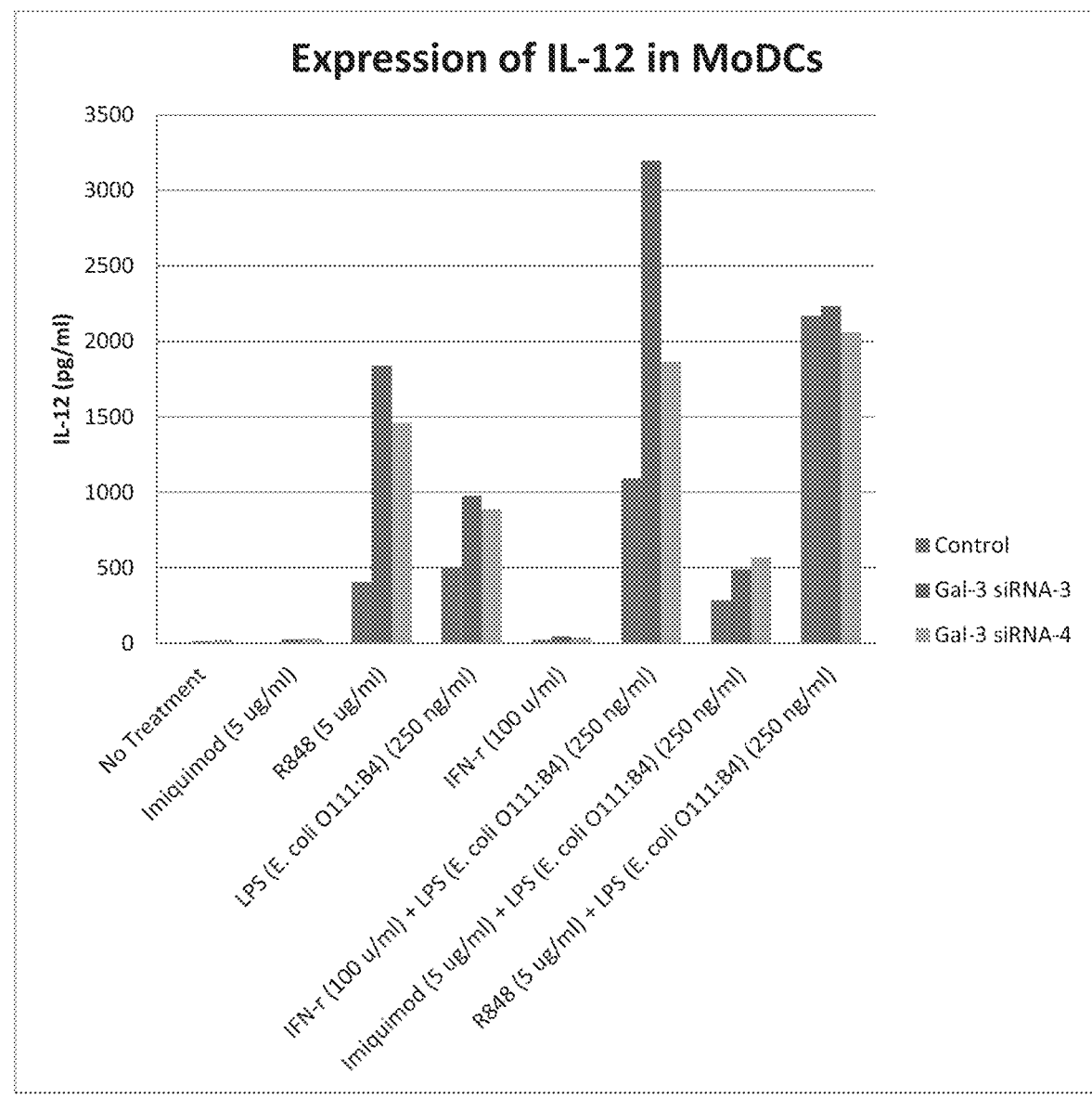

Figure 11B. Galectin-3 knockdown dampens p19 IL-23 production in TLR-stimulated MoDCs
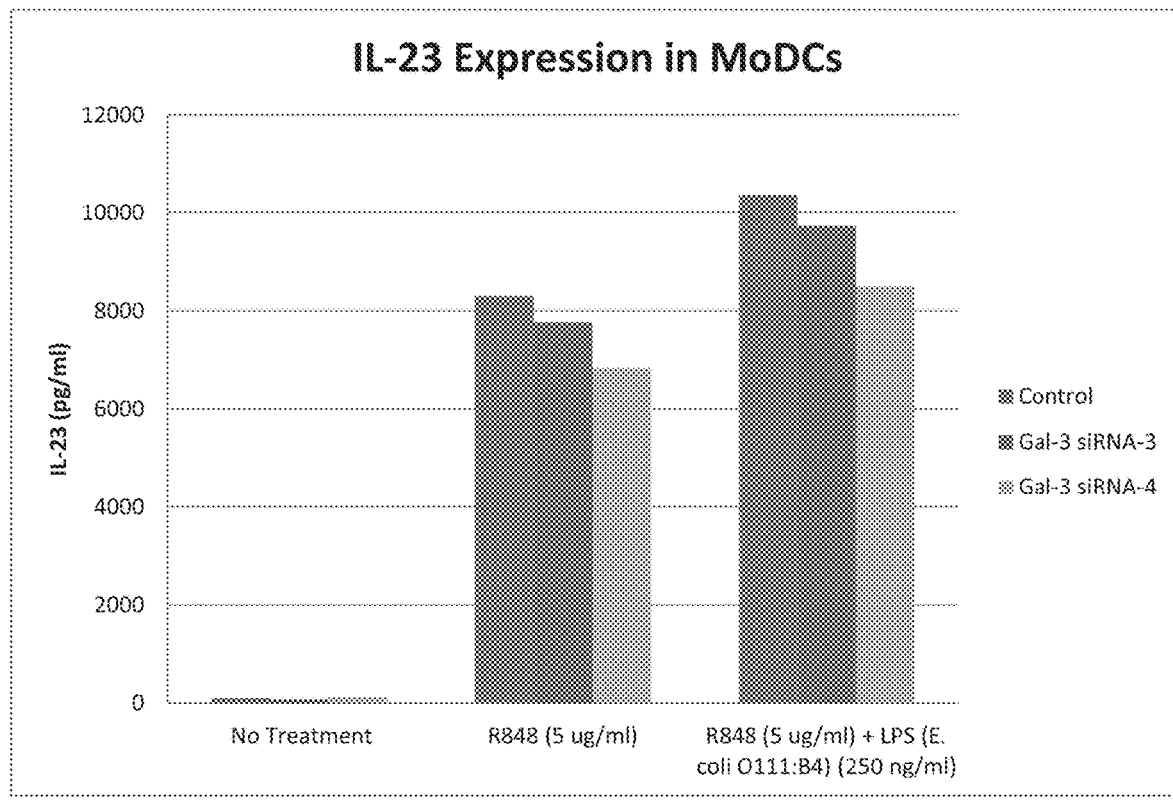

Figure 11C. Galectin-3 knockdown augments IL-10 production in TLR-stimulated MoDCs
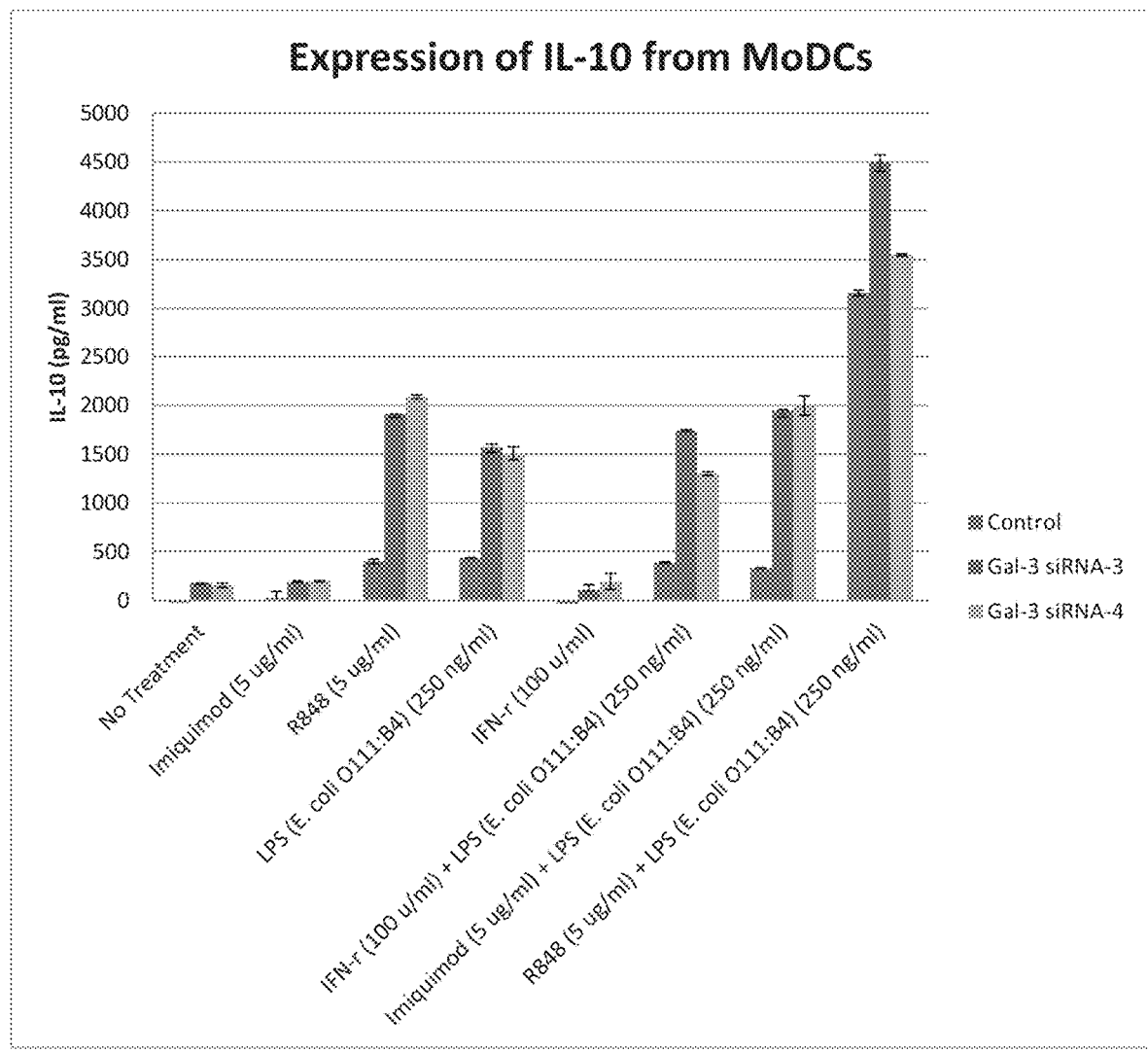

Figure 11D. Effect of galectin-3 knockdown on TGF-β production in TLR-stimulated MoDCs
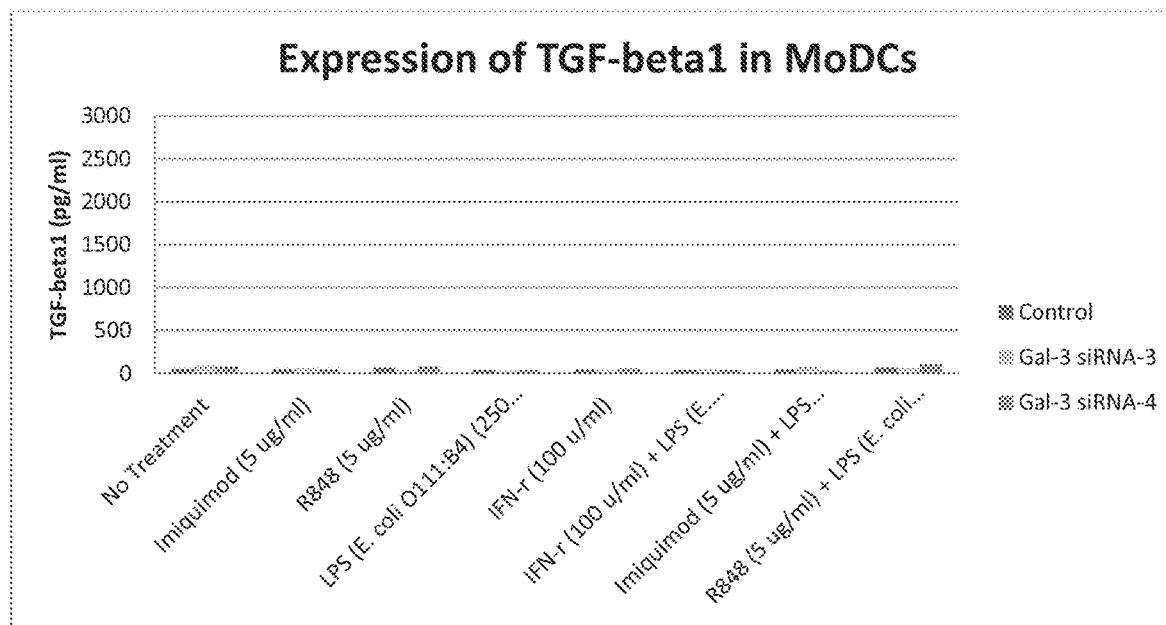

Figure 12A. Galectin-3 knockdown upregulates p35 IL-12 messages in TLR-stimulated MoDCs
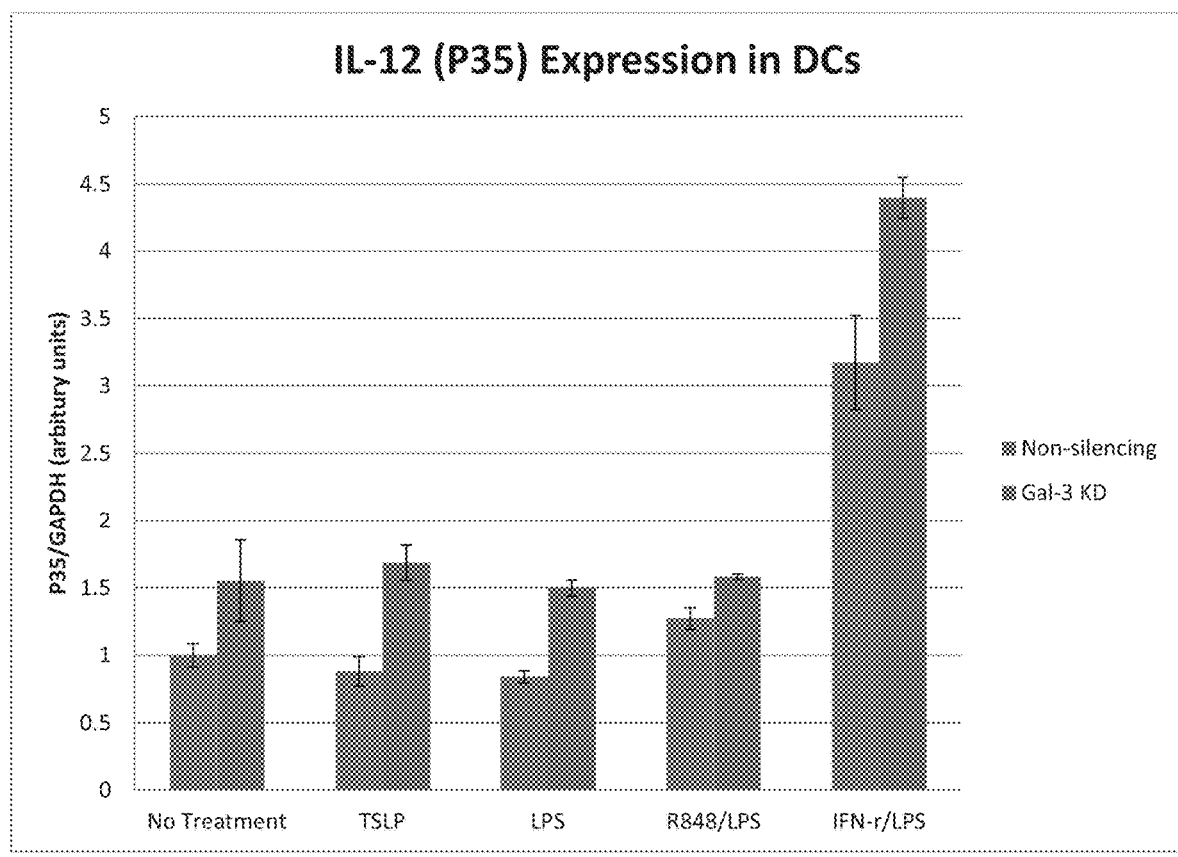

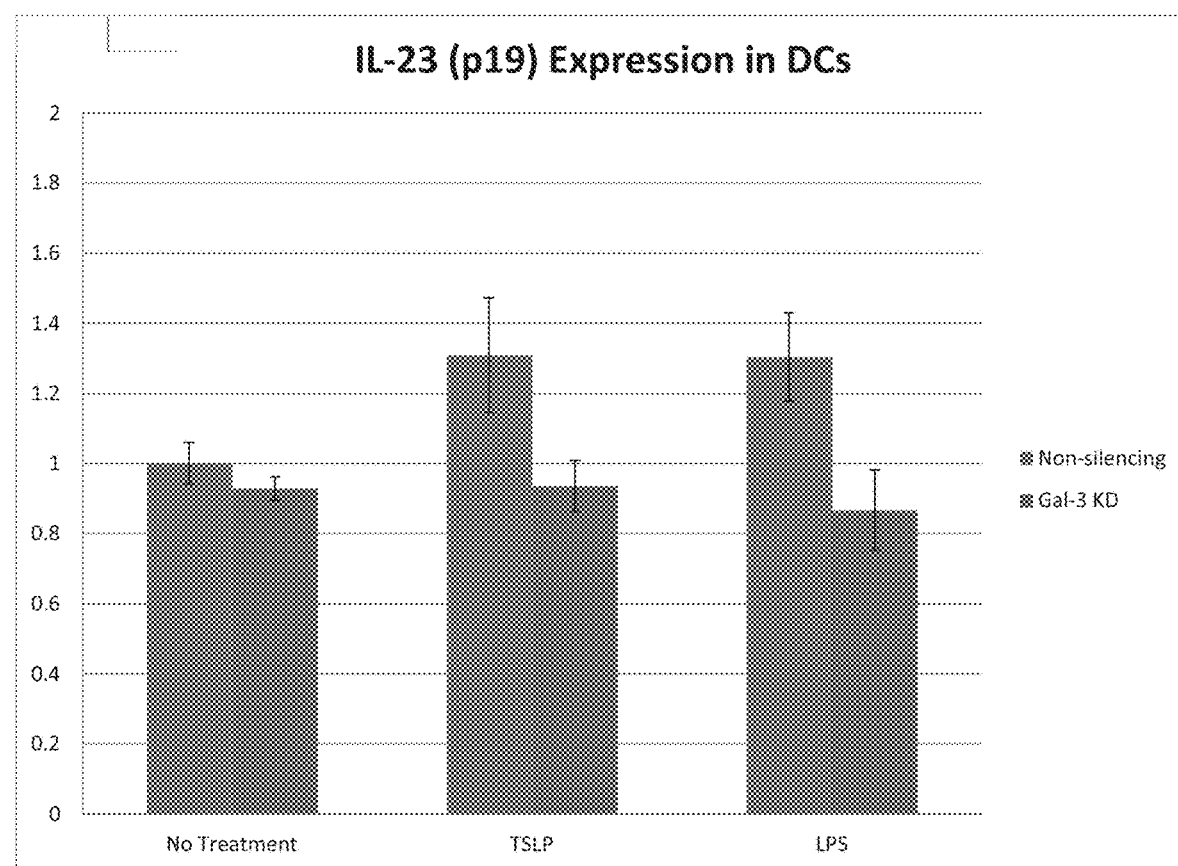
Figure 12B. Downregulation of p19 IL-23 message in TLR-stimulated MoDCs Figure 13. Gaectin-3 knockdown potentiates IL-10 production by macrophages in obese tissues, and alleviates obesity-induced inflammation, insulin resistance and T2D
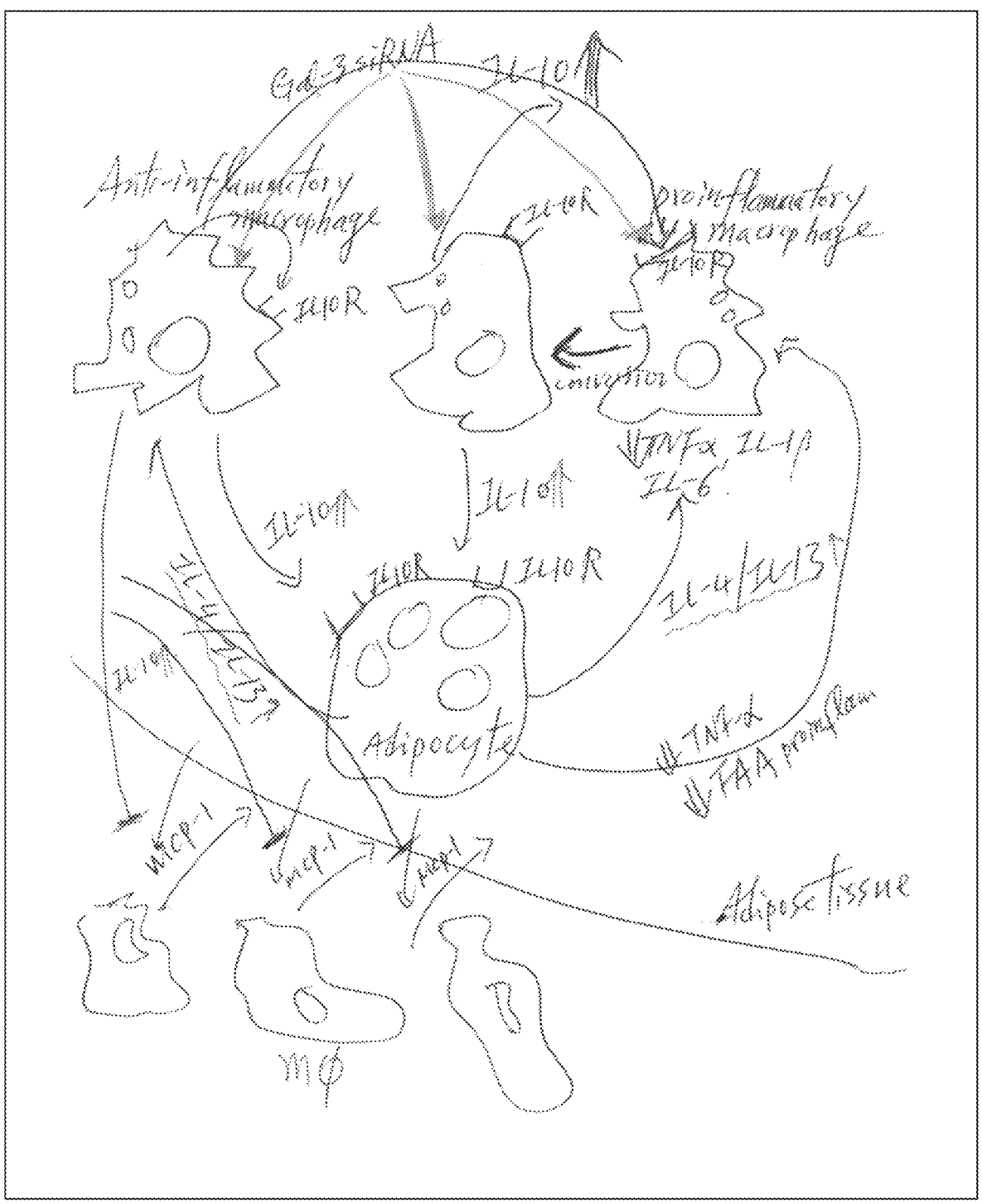

SEQUENCE LISTING

<160> NUMBER OF SEQ ID NOS: 61

<210> SEQ ID NO 1
<211> LENGTH: 19
<212> TYPE: RNA
<213> ORGANISM: Homo sapiens

<400> SEQUENCE: 1
gaacaacagg agagucauu                                                19

<210> SEQ ID NO 2
<211> LENGTH: 19
<212> TYPE: RNA
<213> ORGANISM: Homo sapiens

<400> SEQUENCE: 2
cccaaacccu caaggauau                                                19

<210> SEQ ID NO 3
<211> LENGTH: 19
<212> TYPE: RNA
<213> ORGANISM: Homo sapiens

<400> SEQUENCE: 3
gcugaccacu ucaagguug                                                19

<210> SEQ ID NO 4
<211> LENGTH: 25
<212> TYPE: RNA
<213> ORGANISM: Homo sapiens

<400> SEQUENCE: 4
gggaaugaug uugccuucca cuuua                                         25

<210> SEQ ID NO 5
<211> LENGTH: 19
<212> TYPE: RNA
<213> ORGANISM: Homo sapiens

<400> SEQUENCE: 5
aaugacucuc cuguuguuc                                                19

<210> SEQ ID NO 6

```
<211> LENGTH: 19
<212> TYPE: RNA
<213> ORGANISM: Homo sapiens

<400> SEQUENCE: 6
auauccuuga ggguuuggg                                                  19

<210> SEQ ID NO 7
<211> LENGTH: 19
<212> TYPE: RNA
<213> ORGANISM: Homo sapiens

<400> SEQUENCE: 7
caaccuugaa guggucagc                                                  19

<210> SEQ ID NO 8
<211> LENGTH: 25
<212> TYPE: RNA
<213> ORGANISM: Homo sapiens

<400> SEQUENCE: 8
uaaaguggaa ggcaacauca uuccc                                           25

<210> SEQ ID NO 9
<211> LENGTH: 21
<212> TYPE: RNA
<213> ORGANISM: Homo sapiens

<400> SEQUENCE: 9
gggccacuga uugugccuua u                                               21

<210> SEQ ID NO 10
<211> LENGTH: 21
<212> TYPE: RNA
<213> ORGANISM: Homo sapiens

<400> SEQUENCE: 10
ggccacugau ugugccuuau a                                               21

<210> SEQ ID NO 11
<211> LENGTH: 21
<212> TYPE: RNA
<213> ORGANISM: Homo sapiens

<400> SEQUENCE: 11
gccacugauu gugccuuaua a                                               21

<210> SEQ ID NO 12
<211> LENGTH: 21
<212> TYPE: RNA
<213> ORGANISM: Homo sapiens

<400> SEQUENCE: 12
gugccuuaua accugccuuu g                                               21

<210> SEQ ID NO 13
<211> LENGTH: 21
<212> TYPE: RNA
<213> ORGANISM: Homo sapiens

<400> SEQUENCE: 13
gccuuauaac cugccuuugc c                                               21
```

```
<210> SEQ ID NO 14
<211> LENGTH: 21
<212> TYPE: RNA
<213> ORGANISM: Homo sapiens

<400> SEQUENCE: 14
gugccucgca ugcugauaac a                                              21

<210> SEQ ID NO 15
<211> LENGTH: 21
<212> TYPE: RNA
<213> ORGANISM: Homo sapiens

<400> SEQUENCE: 15
gccucgcaug cugauaacaa u                                              21

<210> SEQ ID NO 16
<211> LENGTH: 21
<212> TYPE: RNA
<213> ORGANISM: Homo sapiens

<400> SEQUENCE: 16
acccacgcuu caaugagaac a                                              21

<210> SEQ ID NO 17
<211> LENGTH: 21
<212> TYPE: RNA
<213> ORGANISM: Homo sapiens

<400> SEQUENCE: 17
gcuucaauga gaacaacagg a                                              21

<210> SEQ ID NO 18
<211> LENGTH: 21
<212> TYPE: RNA
<213> ORGANISM: Homo sapiens

<400> SEQUENCE: 18
gaacaacagg agagucauug u                                              21

<210> SEQ ID NO 19
<211> LENGTH: 19
<212> TYPE: RNA
<213> ORGANISM: Homo sapiens

<400> SEQUENCE: 19
agucauuguu ugcaauaca                                                 19

<210> SEQ ID NO 20
<211> LENGTH: 19
<212> TYPE: RNA
<213> ORGANISM: Homo sapiens

<400> SEQUENCE: 20
ccacgcuuca augagaaca                                                 19

<210> SEQ ID NO 21
<211> LENGTH: 19
<212> TYPE: RNA
<213> ORGANISM: Homo sapiens

<400> SEQUENCE: 21
ugcucacuug uugcaguac                                                 19
```

```
<210> SEQ ID NO 22
<211> LENGTH: 19
<212> TYPE: RNA
<213> ORGANISM: Homo sapiens

<400> SEQUENCE: 22
acggugaagc ccaaugcaa                                              19

<210> SEQ ID NO 23
<211> LENGTH: 19
<212> TYPE: RNA
<213> ORGANISM: Homo sapiens

<400> SEQUENCE: 23
agguuucaug uucacugug                                              19

<210> SEQ ID NO 24
<211> LENGTH: 19
<212> TYPE: RNA
<213> ORGANISM: Homo sapiens

<400> SEQUENCE: 24
ugggaauuuc uggugacau                                              19

<210> SEQ ID NO 25
<211> LENGTH: 19
<212> TYPE: RNA
<213> ORGANISM: Homo sapiens

<400> SEQUENCE: 25
gagagucauu guuugcaau                                              19

<210> SEQ ID NO 26
<211> LENGTH: 19
<212> TYPE: RNA
<213> ORGANISM: Homo sapiens

<400> SEQUENCE: 26
acaaucaucg gguuaaaaa                                              19

<210> SEQ ID NO 27
<211> LENGTH: 21
<212> TYPE: RNA
<213> ORGANISM: Homo sapiens

<400> SEQUENCE: 27
auaaggcaca aucaguggcc c                                           21

<210> SEQ ID NO 28
<211> LENGTH: 21
<212> TYPE: RNA
<213> ORGANISM: Homo sapiens

<400> SEQUENCE: 28
uauaaggcac aaucaguggc c                                           21

<210> SEQ ID NO 29
<211> LENGTH: 21
<212> TYPE: RNA
<213> ORGANISM: Homo sapiens

<400> SEQUENCE: 29
uuauaaggca caaucagugg c                                           21
```

<210> SEQ ID NO 30
<211> LENGTH: 21
<212> TYPE: RNA
<213> ORGANISM: Homo sapiens

<400> SEQUENCE: 30
caaaggcagg uuauaaggca c         21

<210> SEQ ID NO 31
<211> LENGTH: 21
<212> TYPE: RNA
<213> ORGANISM: Homo sapiens

<400> SEQUENCE: 31
ggcaaaggca gguuauaagg c         21

<210> SEQ ID NO 32
<211> LENGTH: 21
<212> TYPE: RNA
<213> ORGANISM: Homo sapiens

<400> SEQUENCE: 32
uguuaucagc augcgaggca c         21

<210> SEQ ID NO 33
<211> LENGTH: 21
<212> TYPE: RNA
<213> ORGANISM: Homo sapiens

<400> SEQUENCE: 33
auuguuauca gcaugcgagg c         21

<210> SEQ ID NO 34
<211> LENGTH: 21
<212> TYPE: RNA
<213> ORGANISM: Homo sapiens

<400> SEQUENCE: 34
uguucucauu gaagcguggg u         21

<210> SEQ ID NO 35
<211> LENGTH: 21
<212> TYPE: RNA
<213> ORGANISM: Homo sapiens

<400> SEQUENCE: 35
uccuguuguu cucauugaag c         21

<210> SEQ ID NO 36
<211> LENGTH: 21
<212> TYPE: RNA
<213> ORGANISM: Homo sapiens

<400> SEQUENCE: 36
acaaugacuc uccuguuguu c         21

<210> SEQ ID NO 37
<211> LENGTH: 19
<212> TYPE: RNA
<213> ORGANISM: Homo sapiens

<400> SEQUENCE: 37
uguauugcaa acaaugacu                                           19

<210> SEQ ID NO 38
<211> LENGTH: 19
<212> TYPE: RNA
<213> ORGANISM: Homo sapiens

<400> SEQUENCE: 38
uguucucauu gaagcgugg                                           19

<210> SEQ ID NO 39
<211> LENGTH: 19
<212> TYPE: RNA
<213> ORGANISM: Homo sapiens

<400> SEQUENCE: 39
guacugcaac aagugagca                                           19

<210> SEQ ID NO 40
<211> LENGTH: 19
<212> TYPE: RNA
<213> ORGANISM: Homo sapiens

<400> SEQUENCE: 40
uugcauuggg cuucaccgu                                           19

<210> SEQ ID NO 41
<211> LENGTH: 19
<212> TYPE: RNA
<213> ORGANISM: Homo sapiens

<400> SEQUENCE: 41
cacagugaac augaaaccu                                           19

<210> SEQ ID NO 42
<211> LENGTH: 19
<212> TYPE: RNA
<213> ORGANISM: Homo sapiens

<400> SEQUENCE: 42
augucaccag aaauuccca                                           19

<210> SEQ ID NO 43
<211> LENGTH: 19
<212> TYPE: RNA
<213> ORGANISM: Homo sapiens

<400> SEQUENCE: 43
auugcaaaca augacucuc                                           19

<210> SEQ ID NO 44
<211> LENGTH: 19
<212> TYPE: RNA
<213> ORGANISM: Homo sapiens

<400> SEQUENCE: 44
uuuuuaaccc gaugauugu                                           19

<210> SEQ ID NO 45
<211> LENGTH: 753
<212> TYPE: DNA
<213> ORGANISM: Homo sapiens

<400> SEQUENCE: 45

```
atggcagaca atttttcgct ccatgatgcg ttatctgggt ctggaaaccc aaaccctcaa      60
ggatggcctg gcgcatgggg gaaccagcct gctggggcag ggggctaccc aggggcttcc     120
tatcctgggg cctaccccgg gcaggcaccc caggggcttc atcctggaca ggcacctcca     180
ggcgcctacc ctggagcacc tggagcttat cccggagcac ctgcacctgg agtctaccca     240
gggccaccca gcggccctgg gcctaccca tcttctggac agccaagtgc caccggagcc      300
taccctgcca ctggccccta tggcgcccct gctgggccac tgattgtgcc ttataacctg     360
cctttgcctg ggggagtggt gcctcgcatg ctgataacaa ttctgggcac ggtgaagccc     420
aatgcaaaca gaattgcttt agatttccaa agagggaatg atgttgcctt ccactttaac     480
ccacgcttca atgagaacaa caggagagtc attgtttgca atacaaagct ggataataac     540
tggggaaggg aagaaagaca gtcggttttc ccatttgaaa gtgggaaacc attcaaaata     600
caagtactgg ttgaacctga ccacttcaag gttgcagtga atgatgctca cttgttgcag     660
tacaatcatc gggttaaaaa actcaatgaa atcagcaaac tgggaatttc tggtgacata     720
gacctcacca gtgcttcata ccatgata taa                                    753
```

`<210>` SEQ ID NO 46
`<211>` LENGTH: 1017
`<212>` TYPE: DNA
`<213>` ORGANISM: Homo sapiens

`<400>` SEQUENCE: 46

```
gagtatttga ggctcggagc caccgccccg ccggcgcccg cagcacctcc tcgccagcag      60
ccgtccggag ccagccaacg agcggaaaat ggcagacaat ttttcgctcc atgatgcgtt     120
atctgggtct ggaaacccaa accctcaagg atggcctggc gcatggggga accagcctgc     180
tggggcaggg gctacccag gggcttccta tcctggggcc taccccggc aggcaccccc      240
aggggcttat cctggacagg cacctccagg cgcctaccct ggagcacctg gagcttatcc     300
cggagcacct gcacctggag tctacccagg gccacccagc ggccctgggg ctacccatc     360
ttctggacag ccaagtgcca ccggagccta ccctgccact ggcccctatg gcgcccctgc     420
tgggccactg attgtgcctt ataacctgcc tttgcctggg ggagtggtgc ctcgcatgct     480
gataacaatt ctgggcacgg tgaagccaa tgcaaacaga attgctttag atttccaaag     540
agggaatgat gttgccttcc actttaaccc acgcttcaat gagaacaaca ggagagtcat     600
tgtttgcaat acaaagctgg ataataactg ggaagggaa gaaagacagt cggttttccc     660
atttgaaagt gggaaaccat tcaaaataca agtactggtt gaacctgacc acttcaaggt     720
tgcagtgaat gatgctcact tgttgcagta caatcatcgg gttaaaaaac tcaatgaaat     780
cagcaaactg ggaatttctg gtgacataga cctcaccagt gcttcatata ccatgatata     840
atctgaaagg ggcagattaa aaaaaaaaa agaatctaaa ccttacatgt gtaaaggttt     900
catgttcact gtgagtgaaa ttttttacat tcatcaatat ccctcttgta agtcatctac     960
ttaataaata ttacagtgaa ttacctgtct caatatgtca aaaaaaaaaa aaaaaaa      1017
```

`<210>` SEQ ID NO 47
`<211>` LENGTH: 250
`<212>` TYPE: PRT
`<213>` ORGANISM: Homo sapiens

`<400>` SEQUENCE: 47

```
Met Ala Asp Asn Phe Ser Leu His Asp Ala Leu Ser Gly Ser Gly Asn
1               5                   10                  15
```

```
Pro Asn Pro Gln Gly Trp Pro Gly Ala Trp Gly Asn Gln Pro Ala Gly
         20                  25                  30

Ala Gly Gly Tyr Pro Gly Ala Ser Tyr Pro Gly Ala Tyr Pro Gly Gln
             35                  40                  45

Ala Pro Pro Gly Ala Tyr Pro Gly Gln Ala Pro Pro Gly Ala Tyr Pro
 50                  55                  60

Gly Ala Pro Gly Ala Tyr Pro Gly Ala Pro Gly Val Tyr Pro
 65                  70                  75                  80

Gly Pro Pro Ser Gly Pro Gly Ala Tyr Pro Ser Ser Gly Gln Pro Ser
                 85                  90                  95

Ala Pro Gly Ala Tyr Pro Ala Thr Gly Pro Tyr Gly Pro Ala Gly
             100                 105                 110

Pro Leu Ile Val Pro Tyr Asn Leu Pro Leu Pro Gly Gly Val Val Pro
             115                 120                 125

Arg Met Leu Ile Thr Ile Leu Gly Thr Val Lys Pro Asn Ala Asn Arg
 130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Arg Gln Ser Val Phe Pro Phe
             180                 185                 190

Glu Ser Gly Lys Pro Phe Lys Ile Gln Val Leu Val Glu Pro Asp His
             195                 200                 205

Phe Lys Val Ala Val Asn Asp Ala His Leu Leu Gln Tyr Asn His Arg
 210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Asn Met Ile
                 245                 250

<210> SEQ ID NO 48
<211> LENGTH: 795
<212> TYPE: DNA
<213> ORGANISM: Mus musculus

<400> SEQUENCE: 48
atggcagaca gcttttcgct taacgatgcc ttagctggct ctggaaaccc aaaccctcaa      60
ggatatccgg gtgcatgggg gaaccagcct ggggcagggg gctacccagg gctgcttat     120 cctggggcct acccaggaca agctcctcca ggggcctacc caggacaggc tcctccaggg     180
gcctacccag acaggctcc tcctagtgcc taccccggcc caactgcccc tggagcttat     240
cctggcccaa ctgccctgg agcttatcct ggctcaactg ccctggagc cttcccaggg     300 caacctgggg cacctggggc ctaccccagt gctcctggag ctatcctgc tgctggccct     360 tatggtgtcc ccgctggacc actgacggtg ccctatgacc tgcccttgcc tggaggagtc     420
atgccccgca tgctgatcac aatcatgggc acagtgaaac ccaacgcaaa caggattgtt     480
ctagatttca ggagagggaa tgatgttgcc ttccacttta accccgcttc aatgagaac     540 aacaggagag tcattgtgtg taacacgaag caggacaata ctggggaaa ggaagaaaga     600 cagtcagcct tccccttga gagtggcaaa ccattcaaaa tacaagtcct ggttgaagct     660
gaccacttca aggttgcggt caacgatgct cacctactgc agtacaacca tcggatgaag     720
aacctccggg aaatcagcca actggggatc agtggtgaca taaccctcac cagcgctaac     780
```
cacgccatga tctaa                                                                                     795

<210> SEQ ID NO 49
<211> LENGTH: 264
<212> TYPE: PRT
<213> ORGANISM: Mus musculus

<400> SEQUENCE: 49

Met Ala Asp Ser Phe Ser Leu Asn Asp Ala Leu Ala Gly Ser Gly Asn
1               5                   10                  15

Pro Asn Pro Gln Gly Tyr Pro Gly Ala Trp Gly Asn Gln Pro Gly Ala
            20                  25                  30

Gly Gly Tyr Pro Gly Ala Ala Tyr Pro Gly Ala Tyr Pro Gly Gln Ala
        35                  40                  45

Pro Pro Gly Ala Tyr Pro Gly Gln Ala Pro Pro Gly Ala Tyr Pro Gly
    50                  55                  60

Gln Ala Pro Pro Ser Ala Tyr Pro Gly Pro Thr Ala Pro Gly Ala Tyr
65                  70                  75                  80

Pro Gly Pro Thr Ala Pro Gly Ala Tyr Pro Gly Ser Thr Ala Pro Gly
                85                  90                  95

Ala Phe Pro Gly Gln Pro Gly Ala Pro Gly Ala Tyr Pro Ser Ala Pro
            100                 105                 110

Gly Gly Tyr Pro Ala Ala Gly Pro Tyr Gly Val Pro Ala Gly Pro Leu
        115                 120                 125

Thr Val Pro Tyr Asp Leu Pro Leu Pro Gly Gly Val Met Pro Arg Met
    130                 135                 140

Leu Ile Thr Ile Met Gly Thr Val Lys Pro Asn Ala Asn Arg Ile Val
145                 150                 155                 160

Leu Asp Phe Arg Arg Gly Asn Asp Val Ala Phe His Phe Asn Pro Arg
                165                 170                 175

Phe Asn Glu Asn Asn Arg Arg Val Ile Val Cys Asn Thr Lys Gln Asp
            180                 185                 190

Asn Asn Trp Gly Lys Glu Glu Arg Gln Ser Ala Phe Pro Phe Glu Ser
        195                 200                 205

Gly Lys Pro Phe Lys Ile Gln Val Leu Val Glu Ala Asp His Phe Lys
    210                 215                 220

Val Ala Val Asn Asp Ala His Leu Leu Gln Tyr Asn His Arg Met Lys
225                 230                 235                 240

Asn Leu Arg Glu Ile Ser Gln Leu Gly Ile Ser Gly Asp Ile Thr Leu
                245                 250                 255

Thr Ser Ala Asn His Ala Met Ile
            260

<210> SEQ ID NO 50
<211> LENGTH: 20
<212> TYPE: RNA
<213> ORGANISM: Homo sapiens

<400> SEQUENCE: 50
ggaaugaugu ugccuuccac                                                                                 20

<210> SEQ ID NO 51
<211> LENGTH: 20
<212> TYPE: RNA
<213> ORGANISM: Homo sapiens

<400> SEQUENCE: 51

-continued

| | |
|---|---|
| cugcaaccuu gaagugguca | 20 |

<210> SEQ ID NO 52
<211> LENGTH: 20
<212> TYPE: RNA
<213> ORGANISM: Homo sapiens

<400> SEQUENCE: 52

| | |
|---|---|
| cccuucauug accucaacua | 20 |

<210> SEQ ID NO 53
<211> LENGTH: 19
<212> TYPE: RNA
<213> ORGANISM: Homo sapiens

<400> SEQUENCE: 53

| | |
|---|---|
| ccuucuccau gguggugaa | 19 |

<210> SEQ ID NO 54
<211> LENGTH: 20
<212> TYPE: RNA
<213> ORGANISM: Homo sapiens

<400> SEQUENCE: 54

| | |
|---|---|
| cuccagaccc aggaauguuc | 20 |

<210> SEQ ID NO 55
<211> LENGTH: 21
<212> TYPE: RNA
<213> ORGANISM: Homo sapiens

<400> SEQUENCE: 55

| | |
|---|---|
| aucucuucag aagugcaagg g | 21 |

<210> SEQ ID NO 56
<211> LENGTH: 21
<212> TYPE: RNA
<213> ORGANISM: Homo sapiens

<400> SEQUENCE: 56

| | |
|---|---|
| auguucccca uauccagugu g | 21 |

<210> SEQ ID NO 57
<211> LENGTH: 20
<212> TYPE: RNA
<213> ORGANISM: Homo sapiens

<400> SEQUENCE: 57

| | |
|---|---|
| gcucccugu gaaaauaucc g | 20 |

<210> SEQ ID NO 58
<211> LENGTH: 20
<212> TYPE: RNA
<213> ORGANISM: Homo sapiens

<400> SEQUENCE: 58

| | |
|---|---|
| gcgagaagau gacccagauc | 20 |

<210> SEQ ID NO 59
<211> LENGTH: 19
<212> TYPE: RNA
<213> ORGANISM: Homo sapiens

<400> SEQUENCE: 59

-continued

```
ccagugguac ggccagagg                                          19

<210> SEQ ID NO 60
<211> LENGTH: 10
<212> TYPE: RNA
<213> ORGANISM: Homo sapiens

<400> SEQUENCE: 60
uuggauccaa                                                    10

<210> SEQ ID NO 61
<211> LENGTH: 22
<212> TYPE: RNA
<213> ORGANISM: Homo sapiens

<400> SEQUENCE: 61
aucucgcuug ggcgagagua ag                                      22
```

RNA INTERFERENCE OF GALECTIN-3 EXPRESSION AND METHODS OF USE THEREOF

FIELD OF INVENTION

The present invention relates to the field of RNA interference (RNAi) and compound delivery. More specifically, the present invention relates to the field of small interfering RNAs (siRNAs) and short hairpin RNAs (shRNAs) and their delivery by non-viral and viral methods. siRNAs and shRNAs mediate downregulation of gene expression and protein expression of galectin-3, and the genes affected by galectin-3 thereof, in the ER stress gene families: upregulated XBP1 and downstream folding enzymes; and cytokine gene families: upregulated IL-12, IL-10 and downregulated IL-23. Therefore, knocking down or RNA interference of galectin-3 can alleviate allergic inflammation, obesity-induced inflammation and type 2 diabetes (T2D) and organ-specific inflammatory diseases in the lung, liver, heart, vasculature and neurons.

BACKGROUND OF INVENTION

Multifunctional Galectin-3

The galectins comprise a family of 14 members of β-galactoside-binding proteins, characterized by their affinity for β-galactosides and by a conserved sequence of the carbohydrate recognition domain that binds to the carbohydrate portion of cell surface glycoproteins or glycolipids. Galectin-3 (Galectin-3, Mac-2, CBP-35, EBP, RL-29, HL-29, L-34, LBP) is a 29-35 kDa chimaera-type galectin (Rabinovich et al. 2002. Trends Immunol. 23:313-320) which is unique in that it is the only member of the galectin family with an extended N-terminal domain constituted of tandem repeats of short amino acid segments (a total of 110-130 amino acids) linked to a single evolutionary conserved, C-terminal carbohydrate-recognition domain (CRD) of about 130 amino acids. Whereas the C-terminal domain is responsible for lectin activity, the presence of the N-terminal domain is necessary for the full biological activity of galectin-3. The binding specificity to ligands is not only determined by the sugar-binding affinity and phosphorylation status of galectin-3 but also by the time and space distribution of their expression and the structure of both the glycan and protein components of the ligand. Galectin-3 containing the NWGR anti-death motif of the Bcl-2 family is involved in regulating apoptosis; galectin-3 also regulates cell cycle, angiogenesis, cell adhesion, oncogenesis, and multiple inflammatory diseases such as allergic diseases, fibrosis, obesity, diabetes and cardiovascular diseases. Galectin-3 is a multi-facet pro-inflammatory mediator, regulating allergic inflammation, such as atopic dermatitis, allergic asthma and rhinitis, obesity-induced diabetic inflammation, myocardial inflammation, atherosclerotic plaque formation, tissue remodeling and macrophage-mediated inflammation in fibrosis.

Galectin-3 Knockdown Therapy for Inflammatory Diseases

A. Allergen-Induced Inflammation

Allergic asthma affects 18 million people in the US, and 38 million people in the major market worldwide. Recent decades have seen considerable increases in the prevalence and severity of allergic asthma. The disease can be differentiated according to severity, innate immunity trigger, involvement of CD4 T-cells, and inflammatory effectors. Allergic rhinitis affects 40 million people in the US. Atopic dermatitis is a chronic, allergic inflammatory skin disease, affecting near 20% children in the US. Etiologies of allergic asthma, rhinitis and atopic dermatitis march like a triad, sharing commonality in disease pathogenesis and treatment. According to conventional disease severity, mild and moderate allergic asthma patients can be adequately controlled with ICS or an ICS/LABA (intranasal corticosteroid/late acting β2-agonist) combination. In contrast, the upper end of moderate to severe, severe asthma and refractory asthma particularly that with neutrophil infiltration mediated by Th17, are corticosteroid-resistant. Severe and refractory patients also suffer from chronic airflow obstructions.

This disease is multifaceted, and has a heterogeneous range of symptoms. A clear picture emerges regarding the pathogenesis of severity of asthma in the past five years. Dendritic cell (DC)-mediated CD4 subset differentiation plays a key role in the pathogenesis of allergic inflammation. In addition to Th2, Th17 plays a key role in moderate to severe and severe asthma. Despite a plethora of drug discovery effort with monoclonal antibodies (MAb) directed against single Th2 cytokine, chemokine or other inflammatory molecule in the past two decades, limited advances were made (except for the anti-IgE drug Xolair). Due to the complexity of allergic inflammation, multiple cytokines have to be influenced, or a molecular hub for multiple cytokines needs be influenced, which lead to a robust protective CD4 T-cell network.

Since the advent of the Th1/Th2 paradigm, the treatment of choice aims at deviating Th2 development by modulating a prominent cytokine or chemokine, critically involved in the disease pathway (Woodcock et al. 2011. NEJM. 364:985-987) The MAb therapy targeting a particularly critical Th2 cytokine leads to disappointment in clinical trials for effort of two-decades. Severe and refractory disease afflicts more than 15% of asthma patients. Interestingly, one product of great promise, anti-IgE targeting IgE (an IL-4/IL-13 switched product) has been launched, although it scores less than 30% efficacies among treated atopic patients with evidently high serum IgE levels. There is high demand for unmet medical needs due to both the number afflicted and its high-risk category. In a rodent animal model, Galectin-3 is implicated in shifting toward the Th2 differentiation in favor of Th2 skewed allergic inflammation (Ge et al. 2010. J. Immunol. 185:1205-1214).

Galectin-3 serves as a molecular hub for multiple inflammatory cytokines in allergic inflammation as shown in the Example 7-9. Gene therapy is a main modality for many disease treatments. And galectin-3 can downregulate for triad allergic inflammation: allergic asthma, rhinitis and atopic dermatitis. Because of multiplicity of cytokines affected by galectin-3, and the key role of DC in regulating CD4 T-cell differentiation, downregulation of galectin-3 or galectin-3 knockdown in DC will favor development of Th1, while concomitantly inhibiting Th2 and Th17 development in alleviating allergic inflammation.

B. Food and Micronutrient-Induced Inflammation: Obesity and Type 2 Diabetes (T2D)

In the United States, obesity (defined as a body mass index greater than 30) is now prevalent in more than 30% of the adult population in the US. The World Health Organization reports that at least one billion adults are overweight and 300 million are obese, and are still to rise. Importantly, the epidemic is affecting children, as the prevalence has tripled in the past 30 years. Despite the complexity of this micronutrient-induced disease, the T2D disease mechanisms are now well known. The seminal work of Hotamisligil and colleagues (L. Glimcher, B. Spiegelman, M. Karin) established JNK as a target of obesity-induced inflammation and insulin resistance, controlled by a crucial ER stress component, XBP1, and the inflammatory cascade is set by excessive ER stressors, JNK and TNF-α stimulation of adipocytes and hepatocytes (Feinstein et al. 1993. JBC. 268:26055-26058; Hirosumi et al. 2002. Nature. 420:333-336; Ozcan et al. 2004. Science. 306:457-461). Galectin-3 is known for preadipocyte proliferation (Kiwaki et al. 2007. Obesity. 15: 32-39). Galectin-3 plays a pro-inflammatory and mediate ER stress. And knocking down galectin-3 expression in critical cell types with respect to ER stress can alleviate inflammation and promote insulin sensitivity. One embodiment of this invention galectin-3 knockdown lays heavy emphasis in activating macrophages to produce high levels of IL-10, which abrogates the action and cellular target of TNF-α.

The ER is a membranous network for regulating protein folding, quality control, trafficking, and targeting. ER can manage metabolic cellular stress for the cell (Todd et al. 2008. Nat. Immunol. 8: 663-674). PERK (PKR-like eukaryotic initiation factor 2a kinase), IRE1α (inositol requiring enzyme 1), and ATF6 (activating transcription factor-6) are the three biochemical arms of ER to handle UPR stress. These three transmembrane proteins are bound by a chaperone, BiP/GRP78, in their intralumenal domains (amino-terminal of IRE1α and PERK and carboxyl-terminal of ATF6) and rendered inactive. Accumulation of improperly folded proteins results in the recruitment of BiP away from these UPR sensors. UPR-induced stress and uptake of micronutrients in the ER lumens result in oligomerization and activation of the two kinases, PERK and IRE1α, and engage a complex downstream signaling pathway. Activation of the third branch of the UPR requires translocation of ATF6 to the Golgi apparatus where it is processed by the serine proteases. ATF6 is reduced in response to ER stress, and the processed monomeric ATF6 eventually reaches the Golgi apparatus, indicating that redox microenvironment is also a potential determinant of ATF6 activation. ATF-6 leads to transcription of immature XBP1 messages. Indeed, activated IRE1α acts as a splicing enzyme for XBP1. Together, appropriate integration of these three arms mitigating ER stress can offer protection of protein homeostasis by (i) reducing protein synthesis, the input folding substrate stress (ii) facilitating protein degradation to alleviate the levels of the substrate for folding, and (iii) enhancing folding efficiency by increased level of protein folding assisting chaperones, and completion of folding that eventually remove the source of UPR stress from the ER lumen.

The harmonious workings of the three arms can result in resolution of crisis of ER stress. Otherwise, the cell is functionally compromised and may undergo abnormal signal transduction and a disease process, obesity-induced inflammation and insulin resistance. Diabetes is an end stage disease wherein β-Langerhans cells, can no longer be protected by PERK arm, and over-production of insulin (to overcome peripheral insulin resistance) renders CHOP-mediated apoptosis, and the pancreas is devoid of insulin secretion. In the middle of the spectrum between harmony and death lies a spectrum of ER-stress mediated abnormal signal transduction and inflammation of various inflamed tissues.

Homeostatic response UPR (ER stress) connects to inflammatory responses by controlling ER stress levels; and modulating inflammation in turn controls ER stress levels. Therefore galectin-3 serves as an optimal target for drug discovery for indication(s) for modulating inflammatory cytokines and signal transducers for modulating ER stress in order to achieve a healthy phenotype for inflammatory diseases. ER stress and inflammation are able to reciprocally activate each other to disrupt normal cell metabolism, and galectin-3 as a modulatory molecular hub or homeostat can play a key role in preventing inflammation-mediated tissue injuries.

ER stress druggable cellular target include metabolic cells such as adipocytes, hepatocytes that can release ER stressor molecules as drivers of homeostasis that communicate with immune cells, i.e., macrophages, DC, CD8+ T-cells, and regulatory CD4+ T-cells via ER stress sensors to either maintain the homeostasis or becomes dysfunctional. For example (FIG. 13 of Example 8), ER stressed adipocytes in turn recruit critically important proinflammatory macrophages that secrete TNF-α, IL-6, and MCP-1, to amplify inflammation (Olefsky and Glass. 2011. Ann. Rev. Phy. 72: 219-246). And TNF-α plays a critical role for insulin resistance in adipocytes, hepatocytes and also myocytes. Importantly, galectin-3 knockdown can provide a down-tuning of the inflammation prone TNF-α producing macrophages by increasing their capacity for IL-10 production. And IL-10 is a master regulatory cytokine (Saraiva et al. 2010. Nat Rev Immunol. 10:170-181) that controls various pro-inflammatory cytokine signal transduction, and notably downstream TNF-α inflammatory events.

In addition, the galectin-3 knockdown can render IL-4/IL-13-sensitized macrophages with a different spectrum of activities, i.e. anti-inflammatory actions, to produce more autocrine IL-10. In the embodiment of this invention, in addition to upregulating IL-10, galectin-3 can control protein folding, i.e., unfolded protein response (UPR), by upregulating XBP1 and downstream ER stress components, critical for resolving obesity-induced inflammation and insulin resistance. Notably, the masterful anti-inflammatory IL-10 acts on multiple targets. Thus in conjunction with moderating ER stress, galectin-3 knockdown creates a favorable change of the internal milieu of inflamed adipose tissues that results in homeostatic feedback for IL-10 producing, anti-inflammatory macrophages for conditioning both macrophages and adipocytes; and anti-inflammatory cytokine-producing adipocytes (IL-4/IL-13) to condition anti-inflammatory macrophages.

DESCRIPTION OF FIGURES AND DRAWINGS

FIG. 1. Knockdown of galectin-3 protein expression in HEK293 by short hairpin (shRNA) shRNA delivered by lentivirus.

Top 10 shRNAs prompted by Invitrogen BLOCK-iT™ RNAi Designer were prepared for this study. The 10 target sequences are: 1). GGGCCACTGATTGTGCCTTAT; 2). GGCCACTGATTGTGCCTTATA; 3). GCCACTGATTGTGCCTTATAA; 4). GTGCCTTATAACCTGCCTTTG; 5). GCCTTATAACCTGCCTTTGCC; 6). GTGCCTCGCATGCTGATAACA; 7). GCCTCGCATGCTGATAACAAT; 8). ACCCACGCTTCAATGAGAACA; 9). GCTTCAATGAGAACAACAGGA; 10). GAACAACAGGAGAGTCATTGT. The ten target sequences, 1, 2, 3, 4, 5, 6, 7, 8, 9, and 10 are represented respectively by SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18) The shRNAs were cloned into lentiviral vector. Lenti-shRNA plasmid DNAs were transfected to HEK293 cells with Lipofectamine 2000 according to manufacturer's protocol and LGALS3 expression levels were determined by western blots 2 days (A) or 4 days (C) after transfection. The relative galectin-3 levels at day2 (B) and day 4 (D) were quantified and normalized to the internal control, α-tubulin. Galectin-3 levels were significantly reduced in all 10 shRNAs 2 days after transfection: nine out of 10 shRNAs reduced galectin-3 levels under 20% of control and five shRNAs even decreased galectin-3 levels beyond 5% of control. At day 4, three shRNAs still kept galectin-3 levels under 10% of control. CK is a non-silencing shRNA that does not target any human or mouse genes, and is used as control. Galectin-3 expression levels were measured after transfection of shRNAs (#11 to 18) from Open Biosystems at day 2 (E) and day 4 (F). Galectin-3 expression was significantly reduced at day 2 after transfection (E), whereas there were no obvious changes of galectin-3 expression at day 4 after transfection, except for shRNA 12 (F).

FIG. 2. Short hairpin RNAs (shRNAs) downregulated galectin-3 transcripts in HEK293 cells HEK293 cells were transfected with shRNAs. The ten shRNA target sequences: 1, 2, 3, 4, 5, 6, 7, 8, 9, and 10 are represented respectively by SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18) Two days (A) or four days (B) after transfection, the total RNAs were isolated via Trizol method (Invitrogen) and used for first-strand cDNA synthesis (ProtoScript® M-MuLV First Strand cDNA Synthesis Kit, NEB). The cDNAs were used for real time quantitative PCR with a pair of LGALS3 specific primers, LGALS3 Q-PCR-Fw (5'-GGAAUGAUGUUGCCUUCCAC-3') (SEQ ID NO:50) and LGALS3 Q-PCR-Rev (5'-CUGCAACC-UUGAAGUGGUCA-3') (SEQ ID NO:51) (Applied Biosystems). SYBR Green qPCR Master Mixture (2×) (Applied Biosystems) was used for PCR reaction. The relative LGALS3 mRNA levels were normalized with the internal control of GAPDH. The two primers for GAPDH are: GAPDH Q-PCR-Fw 5'-CCCUUCAUUGACCUCAACUA-3' (SEQ ID NO:52) and GAPDH Q-PCR-Rev 5'-CCUU-CUCCAUGGUGGUGAA-3' (SEQ ID NO:53). Two days after transfection, 9 out of 10 shRNAs reduced LGALS3 mRNA under 30% of control, 4 of them even under 10% of control. Four days after transfection, 8 shRNAs kept LGALS3 mRNAs under 60% of control, and 2 out of the 8 shRNAs kept LGALS3 mRNA levels under 30% of the control (detailed description with SEQ ID NOs is described in the text of Example 1). CK is a non-silencing shRNA that does not target any human or mouse genes, and is used as control.

FIG. 3. Galectin-3 knockdown altered ER stress protein expression in HEK293 cells Galectin-3 expression was downregulated in HEK293 cells by shRNAs. The ten shRNA target sequences: 1, 2, 3, 4, 5, 6, 7, 8, 9, and 10 are represented respectively by SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18). The effects of knockdown galectin-3 on the expression of ER stress related proteins were measured by western blot. Expression of ER stress marker, BiP, was significantly increased in galectin-3 knockdown cells. ER stress sensor, PERK, and its substrate, eIF2α, had very small change in expression after galectin-3 knockdown. Two ER resident proteins, PDI and ERO1 that enable protein folding as a coupled redox partner, were enhanced after downregulating galectin-3. Calreticulin (CRT) and calnexin are two quality-control chaperones that bind to and edit misfolded proteins, ensuring folded protein transportation from the ER lumens to the Golgi apparatus. The expression levels of calreticulin in shRNAs transfected cells were enhanced, while calnexin levels were variable. CK is a non-silencing scrambled shRNA used as control. The loading control is α-tubulin.

FIG. 4. Galectin-3 knockdown upregulates spliced message of XBP1

HEK293 cells were transfected with siRNA silencing galectin-3 siRNA-4 (SEQ ID NO:8) or scramble siRNA by Lipofectamine RNAiMAX. Cells were harvested 48 hours after transfection, and total RNAs were isolated for RT-PCR. The amplified XBP1 PCR products had two forms: XBP1u and XBP1s. XBP1u is the un-spliced form that is 442 bp in size and contains a Pst I site. After Pst I digestion, the XBP1u generates two fragments, one is about 300 bp and the other one is about 140 bp. In contrast to XBP1u, XBP1s is the spliced form and is 26 nucleotides shorter than XBP1u. Moreover, XBP1s does not contain Pst I site and is resistant to Pst I digestion. Lanes 2 to 6 were RT-PCR product of XBP1 and lanes 8 to 12 were RT-PCR product digested with Pst I. Lanes 1, 7 and 13 were the 100 bp DNA standard. DMSO treated HEK 293 cells were the control of basal level of XBP1 splicing and tunicamycin (1 μg/ml) treated HEK 293 cells were the control of enhanced XBP1 splicing. Galectin-3 knockdown cells had 2-3 folds more spliced XBP1, XBP1s, than that of control (scramble siRNA transfected HEK 293 cells), indicating that IRE-1α was activated after galectin-3 knockdown.

FIG. 5. Galectin-3 knockdown upregulates mature XBP1 protein

HEK293 cells were transfected with siRNA silencing gal-3 siRNA-4 (SEQ ID NO:8) or scramble siRNA by Lipofectamine RNAiMAX. Six hours before harvest, cells were treated with TM at 0.1, 0.5, 1.0, and 5.0 μg/ml, respectively (B). Forty-eight hours after transfection, cells were harvested for protein assay. Lane 1 was no transfection (TM 0.1 ug/ml). Lane 2 was scramble siRNA (TM 0.1 ug/ml). Lane 3 was Galectin-3 siRNA (TM 0.1 ug/ml) . . . . Lane 4 was no transfection (TM 0.5 ug/ml). Lane 5 was scramble siRNA (TM 0.5 ug/ml). Lane 6 was galectin-3 siRNA (TM 0.5 ug/ml). Lane 7 was no transfection (TM 1.0 ug/ml). Lane 8 was scramble siRNA (TM 1.0 ug/ml). Lane 9 was galectin-3 siRNA (TM 1.0 ug/ml). Lane 10 was no transfection (TM 5.0 ug/ml). Lane 11 was scramble siRNA (TM 5.0 ug/ml). Lane 12 was galectin-3 siRNA (TM 5.0 ug/ml). Lane 13 was scramble siRNA (no TM). Lane 14 was galectin-3 siRNA (no TM).

FIG. 6. Diagram of modulation of ER stress by galectin-3 knockdown in alleviating insulin resistance and type 2 diabetes The embodiment of this invention resides in galectin-3 siRNA knockdown therapy in intervening at different levels of key checkpoints of ER stress. siRNA knockdown can improve stress management at three branches of ER stress pathways, while downregulating a key sub-branch of inflammatory pathway. Thus (i) Embodiment of galectin-3 gene therapy can lead a compensatory upregulation of PERK and its downstream eIF2α, ATF-4, Nrf-2 for a more reduced environment, culminating in a lower ROS level. In the Example, the embodiment of galectin-3 knockdown registers a two to three fold increment of PERK activities. (ii) Embodiment of galectin-3 knockdown at levels of enhanced XBP1s. In the Example, the spliced form of XBP1 is enhanced in galectin-3 knockdown therapy, which then leads to upregulated BiP, PDI, ERO1, and CRT. Thus embodiment of upregulated XBP1s is a key checkpoint improved by the gene therapy, and the enhanced folding can alleviate ER stress due to completion of protein folding and reduced UPR oxidative stress. (iii) Embodiment of galectin-3 knockdown therapy resides in fine-tuning of IRE1α. IRE1α serves as the bifurcating point for anti-inflammatory IRE1α associated with XBP1 pathway or leads to activation of ERAD, the UPR degradation pathway. The embodiment of galectin-3 knockdown not only advocates XBP1s accumulation but also is implicated in augmenting ERAD degradation. (iv) Embodiment of galectin-3 knockdown gene therapy at levels of attenuating JNK and IKKβ. Overt IRE1α stimulation leads to a complex IRE1αsome organelle-like complex structure that activates of pro-inflammatory IKKβ and JNK. In Example, galectin-3 siRNA therapy causes attenuation of JNK. It is established that XBP1 and JNK are two critical intervening checkpoints for obesity-induced inflammation, insulin resistance and T2D. Thus the overall embodiment of the invention is the use of galectin-3 knockdown therapy for treating insulin resistance and T2D.

FIG. 7. Cross-species galectin-3 siRNA knocks down endogenous galectin-3 in human MoDCs and RAW264.7 macrophages.

Invitrogen's BLOCK-iT™ RNAi Designer designed four cross-species siRNA. The target sequences of galectin-3 siRNA are: a). siRNA-1: 5'-GAACAACAGGAGAGUCAUU-3' (SEQ ID NO: 1); b). siRNA-2: 5'-CCCAAACC-CUCAAGGAUAU-3' (SEQ ID NO: 2); c). siRNA-3: 5'-GCUGACCACUUCAAGGUUG-3 (SEQ ID NO: 3)'; d). siRNA-4: 5'-UAAAGUGGAAGGCAACAUCAUUCCC-3' (SEQ ID NO:8). Human MoDCs (A) and mouse RAW264.7 cells (B) were knockdown by galectin-3 siRNAs with Invitrogen's Lipofectamine RNAiMAX (according to manufacturer's protocol), and analyzed by western blots. Peripheral blood mononuclear cells (PBMCs) were purified from human blood buffy coat (San Diego Blood Bank) via Ficoll-Hypaque density gradient centrifugation. PBMCs differentiated to immature dendritic cells (iDCs) by co-culturing with GM-CSF and IL-4 for 5 days, and were further stimulated to mature DCs (mDCs) by overnight culturing with IL-1, IL-6, TNF-α, and prostaglandin E2 (PGE2) (Sigma). All the cytokines were purchased from PeproTech. RAW264.7 cells were cultured with DMEM with 10% FBS. MoDCs and RAW264.7 cells were transfected with 4 siRNAs targeting galectin-3 or a Non-targeting siRNA control that does not targeting any human and mouse genes. Two days after transfection, the cells were harvested and used for western blots. Some of the transfected MoDCs were used for FACS analysis.

FIG. 8. Analysis of endogenous galectin-3 by in MoDCs treated with galectin-3 siRNA Peripheral blood mononuclear cells (PBMCs) were purified from human blood buffy coat (San Diego Blood Bank) via Ficoll-Hypaque density gradient centrifugation. PBMCs differentiated to immature dendritic cells (iDCs) by co-culturing with GM-CSF and IL-4 for 5 days, and were further stimulated to mature MoDCs by overnight culturing with maturing media containing IL-1, IL-6, TNF-α, and prostaglandin E2 (PGE2) (Sigma). All the cytokines were purchased from PeproTech. Antibodies of APC-anti-human CD83 (eBioscience) and PE-anti-human CD205 (BioLegend) were used to stain MoDCs (A). To detect intracellular IL-12 and OX40L proteins, brefeldin A (BFA) was added 4 hours before harvest to stop protein secretion. Collected cells were washed with ice-cold 1×PBS, fixed with 2% paraformaldehyde, then, were permeabilized before were stained with antibodies of APC-anti-human IL-12(p35) (R&D Systems) and PE-anti-human OX40L (BioLegend). The stained MoDCs were used for FACS analysis (B). Panel A: x-axis, CD83, y-axis, CD205; Panel B: x-axis, IL-12, y-axis, OX40L. (C). APC-anti-human galectin-3 antibody (R&D Systems) was used to label intracellular galectin-3 protein, Intracellular galectin-3 level was detected by staining with biotinylated antibody against human galectin-3 following with streptavidin-FITC (C). Galectin-3 siRNA knockdown by siRNA-4 (SEQ ID NO:8) in MoDCs was described in example 3. MoDCs were harvested 48 hours after siRNA transfection, and then washed with ice cold 1×PBS with 1% BSA and 1% sodium azide. The cells were resuspended to 1-5×10⁶ cells/ml in 1×PBS with 1% BSA. In a 96-well plate, add 100 μl of the resuspended MoDCs. Fix the cells with 2% paraformaldehyde for 20 minutes at room temperature. Permeabilization Buffer (150 μl) was added to each well, and the 96-well plate was centrifuged at 200 g for 5 minutes. After centrifugation, the supernatants were taken out. The cells were washed with 100 μl permeabilization buffer, and resuspended in 100 μl Permeabilization Buffer. Biotinylated antibody against human galectin-3 was added to the appropriate wells and incubated at room temperature for 20 minutes. After washing with 150 μl permeabilization buffer to each well, streptavidin-FITC was added to the cells with treated with biotinylated antibody against human galectin-3, and incubated at room temperature for 20 minutes. The cells were washed with 150 μl permeabilization Buffer, and centrifuged at 200 g for 5 minutes. After taking out the supernatant, the cells were resuspended in 150 μl 1×PBS/1% BSA, and used for FACS analysis. After galectin-3 siRNA knockdown, 65.2% MoDCs were galectin-3 negative and there were only 34.8% of MoDCs were galectin-3 positive cells (FIG. 8C).

FIG. 9 A-C. Enhanced cytokine expression in MoDC stimulated with TLR ligands

Multiple stimuli, imiquimod, R848, LPS, and IFN-γ, were used alone or as combination to enhance expression of cytokines, IL-12 and IL-23. The secreted IL-12 (A) and IL-23 (B) were quantified by ELISA according to manufacturer's protocols. The ELISA kits for IL-12 and IL-23 were purchase from eBioscience. Imiquimod (In Vivogen) and R848 (In Vivogen) were used alone at 1, 5, and 10 μg/ml, respectively. The combination of imiquimod and R848 were used to treat MoDCs at 1, 5, and 10 μg/ml each, respectively. LPS isolated from three different *E. coli* strains, *E. coli* 026:B6 (Sigma), *E. coli* 0111:B4 (List Biological Laboratories), and *E. coli* 00157:H7 (List Biological Laboratories), were used to stimulate cytokine expression at 50 ng/ml or 1 μg/ml. IFN-γ (PeproTech) alone was used at 100 or 1,000 U/ml. MoDCs were also treated with combination of LPS with IFN-γ, imiquimod, and R848 [IFN-γ (100 U/ml)+LPS (*E. coli* 0111:B4) (10 ng/ml), IFN-γ (100 U/ml)+LPS (*E. coli* 0111:B4) (250 ng/ml), IFN-γ (100 U/ml)+LPS (*E. coli* 00157:H7) (10 ng/ml), IFN-γ (100 U/ml)+LPS (*E. coli* 00157:H7) (250 ng/ml), Imiquimod (5 μg/ml)+LPS (*E. coli* 0111:B4) (250 ng/ml), and R848 (5 μg/ml)+LPS (*E. coli* 0111:B4) (250 ng/ml)]. (C) Real-time PCR was performed for endogenous galectin-3 message in galectin-3 siRNA knockdown MoDC. Total RNAs were isolated and used for cDNA synthesis. LGALS3 mRNA levels were quantified by real-time PCR. Actin was used as an internal control. siRNA reduced LGALS3 mRNA under 30% (no treatment and LPS) or 80% (R848 or R848/LPS) of un-treated control cell. Control is a non-silencing shRNA that does not target any human or mouse genes, and is used as control.

FIG. 10. Diagram of galectin-3 as the molecular hub for controlling multiple cytokine responses in dendritic cells and macrophages in allergic inflammation.

The embodiment of the invention resides in its anti-inflammatory modulation for a combination of cytokines following galectin-3 siRNA treatment. Galectin-3, a proinflammatory molecule, serves as a common hub for relaying multiple cytokines at levels of message expression as well as translated product. (i) Embodiment of galectin-3 knockdown therapy for IL-12 upregulation. Galectin-3 knockdown in MoDC lead to upregulation of the p35 IL-12 message and translated products. IL-12 can tip the immune balance toward Th1 phenotypes and counteract allergic inflammation of predominant Th2 phenotype. (ii) Embodiment of galectin-3 knockdown therapy for augmented IL-10 production. Galectin-3 siRNA knockdown leads to enhanced production of IL-10, which is a major anti-inflammatory cytokine to control allergic inflammation, and importantly obesity-induced inflammation and type 2 diabetes (T2D). IL-10 inhibits multiple inflammatory cytokine production, including TNFα-induced inflammation and signal transduction on macrophages and obese tissues and attenuates insulin resistance. (iii) Embodiment of galectin-3 knockdown in treating allergic inflammation. In contrast, galectin-3 siRNA knockdown can attenuate expression of IL-17A, a prominent cytokine involved in Th17-mediated inflammation in severe asthma and allergic inflammation (and autoimmune diseases). Thus one main aspect of the overall embodiment of the invention is the use of galectin-3 knockdown therapy for treating the triad allergic inflammation, atopic asthma, rhinitis and dermatitis, in particular the anti-inflammatory IL-10, and blunting IL-17 for severe atopic asthma.

FIG. 11. Effect of galectin-3 knockdown on production of cytokines: IL-12, IL-23, IL-10, and TGF-β, in MoDCs MoDCs were transfected with siRNA-3 and 4 (SEQ ID NO:7, and SEQ ID NO:8) targeting galectin-3. The control MoDCs were the cells transfected with non-targeting siRNA. MoDCs were treated with imiquimod (5 μg/ml), R848 (5 μg/ml), LPS (250 ng/ml), IFN-γ (100 U/ml), IFN-γ (100 U/ml)+LPS (250 ng/ml), imiquimod (5 μg/ml)+LPS (250 ng/ml), and R848 (5 μg/ml)+LPS (250 ng/ml). The levels of cytokines, IL-12 (A), IL-23 (B), IL-10 (C), and TGF-β (D), were quantified by ELISA according to manufacturer's protocols. IL-10 ELISA was purchased from eBioscience, and TGF-β ELISA kit was purchased from BioLegend.

FIG. 12. Effect of galectin-3 knockdown on cytokine mRNA levels in MoDCs

MoDCs were transfected with siRNA targeting galectin-3 (SEQ ID NO:8). Non-targeting siRNA was used as control. MoDCs were stimulated with LPS, R848, or R848/LPS for 24 hours before harvesting the cells. The total RNAs were isolated via Trizol method (Invitrogen) and used for first-strand cDNA synthesis (ProtoScript® M-MuLV First Strand cDNA Synthesis Kit, NEB). Real-time PCR was performed to quantify the mRNA levels of IL-12 (p35) (A) and IL-23 (p19) (B). The primers used for p35 are: p35-F (5'-CUCCA-GACCCAGGAAUGUUC-3') (SEQ ID NO:54) and p35-R (5'-AUCUCUUCAGAAGUGCAAGGG-3') (SEQ ID NO:55). Primers used for p19 are: p19-F (5'-AUGUUCCC-CAUAUCCAGUGUG-3') (SEQ ID NO:56) and p19-R (5'-GCUCCCCUGUGAAAAUAUCCG-3') (SEQ ID NO:57). Actin mRNA was used as internal control for RT-PCR. The primers used for actin are: actin-F (5'-GCGAGAAGAUGACCCAGAUC-3') (SEQ ID NO:58) and actin-R (5'-CCAGUGGUACGGCCAGAGG-3') (SEQ ID NO:59). P35 and p19 mRNA levels were normalized to actin mRNA levels.

FIG. 13. Diagram of galectin 3 as the gatekeeper for IL-10, inhibiting obesity-induced inflammation and insulin resistance IL-10 as the master switch for anti-inflammatory macrophages in adipose tissues. Proinflammatory macrophages producing TNF-account for mass of adipocytes that in turn feedback on proinflammatory macrophages to sustain the obesity-induced inflammation and insulin resistance. IL-10 is known to inhibit signal transduction by TNF-α. The embodiment of this invention is to convert proinflammatory macrophages into anti-inflammatory macrophages with high levels of IL-10 production by galectin-3 gene therapy as shown in Example. IL-10 production enhanced by galectin-3 siRNA knockdown plays a key role in sustaining the anti-inflammatory function of macrophages. High levels of IL-10 can then attenuate TNF-α and IL-6 production by proinflammatory macrophages that are converted to assume anti-inflammatory activities. (ii) Attenuation of TNF-α by IL-10 in adipose tissues. Another embodiment of the invention resides in downregulating TNF-α production by adipocytes via exogenous IL-10 produced by galectin-3 knockdown macrophages. Thus the overall embodiment of this invention is to treat obesity and insulin resistance of adipocytes by galectin-3 knockdown in macrophages that produce high levels of IL-10 to counteract proinflammatory macrophages and adipocytes.

DETAILED DESCRIPTION OF INVENTION

A. Galectin-3 Impacted Inflammatory Diseases: Allergic Inflammation

Galectin-3 exhibits affinity for β-galactosides on glycan as well as affinity for consensus amino acids on multiple protein species. A great deal of evidence indicates that endogenous galectin-3 regulates functions of multiple cell types including lymphocytes, and recently also extending to DC and macrophages. It was reported that Th2-mediated allergic asthma and Th17-mediated EAE autoimmune diseases are significantly attenuated in galectin-3 gene deficient mice (Ge et al. 2010. J. Immunol. 1205-1214; Jiang, 2009. J. Immunol. 182: 167-1173).

Understanding mechanisms of allergic inflammation causes a major paradigm shift S disease treatment. New drug development is shifted from the conventional ICS/LABA toward drugs that favoring an overall balanced CD4 T-cell network of the new paradigm. Galectin-3 serves as the gatekeeper or molecular hub for multiple inflammatory and anti-inflammatory cytokines.

A preferred embodiment of the invention resides in knocking down this molecular hub of galectin-3 using small interfering RNA and small hairpin RNA in order to impact multiple critical cytokine pathways at once at levels of DC and/or macrophages. Therefore, galectin-3 knockdown at level of antigen presenting DC and macrophages in turn leads to balance CD4 T-cells toward anti-inflammatory Th1, while deviating from Th2 and Th17 that cause allergic inflammation. The embodiment of galectin-3 knockdown therefore causes a robust conversion from the allergic inflammation phenotype to a disease-free phenotype. Therefore, the embodiment of galectin-3 knockdown via RNA interference provides beneficiary fine-tuning over multiple critical inflammatory and anti-inflammatory cytokines all at once leading to heightened levels of protective Th1, and diminished levels of Th2, and Th17 via one single galectin-3 molecular hub.

Allergic inflammation of various disease types in particular, allergic asthma, is established as a hygiene-related disease (Yazdanbakhsh et al, 2002. Science. 296:490-494). Breach of epithelial cell barriers, and exposure to various bacterial, fungal, viral antigens in particular early in life underlie allergic phenotypes to the encounter of the respiratory allergens. Microbial and environmental allergens (Trompette et al. 2009. Nature. 457:585-588; Eisenbarth et al. 2002. JEM. 196: 1645-1651), i.e., LPS, LPS binding protein (MD2), single and double stranded viral RNA that stimulate TLR4 and/or TLR7/8 on DC and macrophages, play a key role in pathogenesis of allergic inflammation and the triad (allergic) atopic march: asthma, rhinitis and dermatitis. DC strategically located within and beneath the upper/lower airway epithelium, and in particular dermal dendritic cells (DDC) and Langerhans cells (LC) around epidermis, constitute a first-line cellular network along the respiratory and epidermal tracts. In spatiotemporal sequence, airway DC sampling environmental allergens, orchestrate or direct three types of inflammatory CD4 T-cells: Th1, Th2, and Th17 subsets, which in turn determine susceptible vs protective asthma, and allergic inflammation phenotypes.

Galectin-3 knockdown therapy therefore is applicable to and can ameliorate a wide spectrum of allergic inflammatory diseases: such as Th2 and IgE-mediated allergic (atopic) asthma, allergic rhinitis, atopic dermatitis, IgE-mediated food allergy, anaphylaxis, allergic conjunctivitis, and Th2-mediated IgE production. Thus one preferred embodiment of galectin-3 knockdown resides in upregulation of IL-12 in DC and macrophages that cause upregulated Th1, which counteracts Th2-mediated inflammation and IgE production. Another preferred embodiment of galectin-3 knockdown resides in downregulation of IL-23, which attenuates Th17.

Yet another preferred embodiment of the invention resides in upregulation of IL-10, which attenuates Th2 and Th17 and downregulates allergic inflammation; furthermore, IL-10 also attenuates Th1 to prevent excessive Th1 polarization and Th1-mediated inflammation. Therefore the embodiment of galectin-3 knockdown aims at modulating a critical triad cytokine set, IL-12, IL-10, and IL-23 at level of antigen (allergen) presenting DC and macrophages can be achieved all at once via targeting the galectin-3 molecular hub in that robust protective allergic or asthmatic inflammation phenotypes ensues, sustainable by altered CD4 T-cell network. The embodiment of the invention is distinct from the current one-on-one cytokine neutralization approach with monoclonal antibodies (MAb) against one cytokine at Th2 level.

Regarding natural history of allergic inflammatory diseases, LPS and single and double stranded RNA virus are known to exacerbate onset of allergic airway inflammation by activating airway DC and airway epithelium. Therefore an inflammatory stress model is developed with stimulation of the Toll-like receptors 4 and 7, and 8, which mimic asthma exacerbation due to bacteria (a source of LPS for TLR4) and viral infections (viral RNA for TLR7/8). Example 4 showed enablement of galectin-3 knockdown in MoDC; Example 5 showed enablement of galectin-3 knockdown upregulating IL-12, IL-10 production, while downregulating IL-23, when stimulated with TLR4, and TLR7/8 ligands, in monocyte-derived dendritic cells (MoDC).

The stimulation with various TLRs in MoDC followed by galectin-3 knockdown in Example 5, simulate airway or other routes of sensitization to innate pattern recognition with subsequent galectin-3 knockdown treatment option. Notably, IL-10 produced via natural TLR activation in vivo is a masterful anti-inflammatory cytokines for downregulating Th2/Th17 skewed allergic inflammation in the context of natural allergen sensitization via respiratory and gastrointestinal (GI) tracts, skin or hematogenous route, wherein (competent) allergens are likely also to carry TLR-like determinants or contaminated with the natural microbial TLR ligands.

Upon exposure to natural competent allergens, upregulation of IL-12 in the galectin-3 siRNA/shRNA treated patients is critical for counteracting levels of Th2 skewed IL-4/IL-5/IL-13 producing inflammatory Th2. IL-17-mediated severe allergic asthma.

Downregulated galectin-3 also dampens production of IL-23p19 in DC, critical for ameliorating, Th17-mediated severe, refractory asthma in patients. Galectin-3 knockdown in patients will attenuate levels of Th2 and Th17, distributed in the target organs and/or lymphoid tissues, i.e., primary (bone marrow, thymus), secondary lymphoid organs (regional lymph nodes and spleens), skin, respiratory (lung and airway) and GI tracts, systemic (blood) and mucosa-associated lymphoid tissues (MALT).

Thus silencing galectin-3, influencing the hub for the triad cytokines in patients manifesting different types of allergic inflammation (Th2, Th2/Th17, Th2 dependent IgE-mediated inflammation) will produce a beneficial treatment effect on atopic asthma, rhinitis, dermatitis and IgE-mediated allergic inflammation, food allergy, anaphylaxis, conjunctivitis, by tipping the balance of CD4 T-cell development toward Th1, while concomitantly dampening Th2 and Th17. As a masterful cytokine (1), IL-10 produced in vivo due to galectin-3 knockdown therapy performs two separate functions (i) in keeping both Th2, Th17 at bay in the patients; (ii) preventing a spill-over of highly polarized Th1-based inflammation in vivo.

Therefore, unlike the single target approach with MAb against a candidate cytokine, knocking down galectin-3 poses a novel anti-inflammatory network intervention in critically affecting the hub of a triad of essential cytokines of DC that control subsequent CD4 T-cell subsets. In Example 1, 4, and 5, the sequences of galectin-3 siRNA were prepared from identical conserved sequences from both human and mouse species, and were shown effective in knocking down endogenous galectin-3 expression in both rodent and human cells. Thus one aspect of the embodiment of the invention is to cross-test the efficacies of the cross-species anti-galectin-3 siRNA or shRNA candidates in that galectin-3 knockdown therapy is effective across the board of different species, including humans.

The embodiment of this invention by galectin-3 small RNA interference therapy aims at a body of inflammatory, cellular network. On a global scale, an architecture comprising five key layers, i.e., allergen/epithelium/APC/lymphocytes/leukocytes, participates in the pathogenesis of allergic inflammation, including asthma. Any one or multiple layers in combination can cause exacerbations of allergic inflammation, thus explaining the complexity of allergic inflammatory diseases. Layer one, consisting of the allergens carrying competent innate pattern recognition signals; Layer two comprises epithelium (airway, GI tract, skin keratinocytes), the breach of the barrier constitute a major predisposition for allergic inflammation; Layer three comprises DC or macrophages at the environmental interface expressing receptors for innate pattern recognition. Layer four comprising resting CD4 T-cells that upon stimulation by allergen-sensitized DC/macrophages, differentiate into Th1, Th2, Th17 or regulatory cell types; Layer five comprises the multiple effector cell types that amplify the CD4 T-cell mediated inflammatory signals, including mast cells/basophils (IgE-mediated vs. IgE-independent), eosinophils (Th2-mediated), and neutrophils (Th17-mediated). Endothelial cells and fibroblasts can also play important role in modulating allergic inflammation, and moderating tissue fibrotic responses and tissue remodeling. Therefore, a preferred embodiment of galectin-3 knockdown is to impact at any or a combination of the five layer architecture, in modulating the epithelium; the signaling of competent allergen and DC/macrophages (the cytokine hub at APC level); communication between DC/macrophages and CD4 T-cells (cytokine hub at T-cell dichotomy level); direct effect on CD4 T-cells; effector leukocytes such as eosinophils, mast cells, neutrophils.

Th17 driven by IL-23-producing DC plays a key role in not only autoimmune diseases but also a variety of immune mediated inflammatory diseases, including allergic asthma. In humans, the role of Th17 and neutrophilic infiltrates receive increasing attention in moderate to severe and severe asthma, resistant to steroid treatment (Lloyd et Al. 2010. Nat Rev Immunol. 10:838-848). Therefore, a balance of a network of CD4 T-cell interactions, i.e., how Th2, and/or Th17 plays out in the midst of Th1 (or Treg) following dendritic cell signal relay, play an important role in homeostastic CD4 T-cell network conducive or protective for the asthma phenotypes. Therefore an embodiment of this invention resides in downregulating p19 IL-23 production by galectin-3 knockdown DC, thereby to attenuate Th17.

Change in network connectivity initiates a robust conversion from the allergic inflammation phenotype or allergic asthma phenotype to a normal disease-free allergy protective phenotype or asthma-free phenotype. With regard to protecting allergic asthma, the penetrance of the embodied galectin-3 knockdown treatment can be pervasive at both vertical and horizontal levels according to the architecture of five layers. In the modality of topical airway administration, airway epithelium can be impacted with reduced inflammation as the foremost primordial line of innate defense prior to antigen presenting cells such as DC, macrophages. The embodiment of the invention of galectin-3 knockdown in protecting allergic asthma can also entail a global involvement of all five layers of cells, including the surrounding vasculature, interstitial tissues and matrix that provide the "niche" for the immune cellular consternation. Thereby, in particular with allergic asthma, galectin-3 knockdown can not only include modulation of galectin-3 as the cytokine hub (for IL-12, IL-10, and 11-23) but also can control other types of cytokines that await discovery. The embodiment of galectin-3 in ameliorating allergic asthma can be mediated via homeostasis of ER stress via the upregulating central pro-folding XBP1 pathway in a number of cell types, including epithelium, DC/macrophages, CD4 T-cells, eosinophils, mast cells and neutrophils, culminating in attenuation or resolution of allergic asthma and/or other types of allergic inflammation.

The overall embodiment of this invention is to treat human allergic patients in the airway, skin, GI tract, eyes, MALT, and primary and secondary lymphoid tissues via galectin-3 knockdown with siRNA or shRNA prepared in a suitable pharmacological carriers, thereby allergic inflammation is alleviated via cytokine modulation, i.e., single or a triad IL-12, IL-10, IL-23 and/or other cytokines and homeostasis of ER stress.

B. Galectin-3 Impacted Inflammatory Diseases: Obesity-Induced Inflammation/Type 2 Diabetes (T2D)

Linking of ER Stress/UPR to Diabetic Inflammation unfolded protein responses (UPR) are responsible for protein folding, and related to the ER stress thus generated, when in excess lead to inflammation responses. It is clear obesity-induced inflammation, insulin resistance, and type 2 diabetes (T2D) are mediated by inappropriate levels of ER stress of the glucose and insulin sensitive cells, and inflammatory macrophages infiltrating those tissues as a result (Olefsky and Glass. 2011. Ann Rev Phy 72: 219-246). And ER stress causes inflammation and develop insulin resistance. Reciprocally inflammation can cause further ER stress. Seminal study of Hotamisligil indicates this step is critically controlled by activated XBP1 (Ozcan et al. 2004 Science. 306:457-461). Activation of the JNK-AP1 plays a key role in obesity-induced inflammation and insulin action. During ER stress, XBP1 (downstream of IRE1α) activates JNK, transcriptionally regulating several inflammatory genes. The obesity-induced expression of proinflammatory cytokines including TNF-α, IL-6, and MCP-1 is also suppressed in mice lacking JNK, leading to protection from insulin resistance and type 2 diabetes.

When overtly stressed, or without a central integrated stress management, IRE1α and PERK branches of the UPR can also lead to activation of the JNK, and another important pro-inflammatory NF-κB/IKK pathway. This pathway also plays a critical role in the induction of multiple inflammatory mediators, implicated in insulin resistance. UPR caused increased proinflammatory IL-8, IL-6, MCP-1, and TNF-α expression in target cells and recruited macrophages. Thus, dysfunctional UPR in the obese state contributes to insulin resistance through IRE1α-mediated c-Jun N-terminal kinase (JNK) activation, which leads to phosphorylation of insulin receptor substrate-1 (IRS-1) on inhibitory serine residues to account for insulin resistance and later a diabetic state. On the other hand, the increase in insulin sensitivity associated with weight loss is associated with elevated XBP1 and less JNK activation. ER stress and inflammation are able to reciprocally activate each other to disrupt normal cell metabolism.

Therefore, at the central stage of controlling insulin resistance and T2D resides in upregulating XBP1 that in turn moderates downstream transcription factors for effector signal-transducing enzymes. Because of the critical importance of XBP1, the embodiment of this invention is to achieve XBP1 upregulation via galectin-3 knockdown to moderate obesity-induced inflammation and T2D.

Efficiency of protein folding governed by XBP1 plays a critical role in downstream activation of JNK/IKK (Hetz and Glimcher, 2009. Mol. Cell. 35:551-561). Therefore one preferred embodiment of the invention resides in galectin-3 knockdown for improving protein folding function across the spectrum of both the upper stream XBP1 as well downstream products. Protein folding in the ER lumen is facilitated by a number of molecular chaperones, including the glucose-regulated proteins BiP and Grp94, and a variety of folding enzymes such as protein disulfide isomerase (PDI). In the Example 2, galectin-3 knockdown embodies a more efficient protein folding: upregulating XBP1, and its related downstream upregulated foldases such as PDI, and BiP, a glucose regulated protein 68 (GRP 68), ERO1. On the other hand, Ron showed that galectin-3 is dramatically upregulated in PERK or eIF2α knockdown cells.

Thus targeting galectin-3 can clearly improves ER stress and plays a central role in preventing insulin resistance and diabetes. Hence galectin-3 knockdown as shown in Example 2 improves the folding efficiency of UPR (FIG. 3) by affecting the pivotal branch of XBP1. In this Example, we show that galectin-3 knockdown enhances protective good ER stress by upregulating the mature form of XBP1 (FIG. 4), and strengthens integrated ER stress management in favor of protein folding to remove futile cycles of unproductive folding which generates excessive ER stress and its related signal transduction pathway (JNK), one of this checkpoint as shown in our data is the galectin-3 and controlling this important branch checkpoint, can in turn improve homeostasis.

Therefore a preferred embodiment of the invention in knocking down galectin-3 and the related XBP1 upregulation is a key ingredient of the druggable target. In another embodiment, the critical role of XBP1 in alleviating insulin resistance is confirmed from another perspective due to enhanced translocation by the regulatory PI3K subunit, p85α since its deficiency leads to attenuated XBP1, and insulin resistance. Galectin-3 knockdown is therefore strongly implicated in attenuating the overall IRE-1a-activation cascade, in that IRE1α under homeostasis is united mainly XBP1 without entering the IRE-1some's phase of in a large molecular assembly uniting with IKK, TRAF2, which activates JNK (Hetz and Glimcher, 2009. Mol. Cell. 35:551-561). Therefore another preferred embodiment of this invention is to implicate a role galectin-3 in upstaging p85α, which causes enhanced XBP1 for alleviating insulin resistance.

Inflammatory Macrophages to Sustain Obesity and Insulin Resistance

Chronic inflammation of adipose tissue with macrophages involvement is related to ER stress. Inflammation can also occur in the liver and pancreas pointing to a link of inflammation and metabolic pathways. ER stress druggable target cells include metabolic cells such as adipocytes, hepatocytes, β-Langerhans cells that can release ER stressor molecules as driver of homeostasis that communicates with immune cells via their ER stress sensors to maintain the homeostasis or become dysfunctional. TNF-α, IL-6, and MCP-1 are mainly secreted by macrophages which causing insulin resistance (Olefsky and Glass. 2011. Ann Rev Phy 72: 219-264). Macrophages are one of the most important second-line effector cells in relaying two way communications with ER over-stressed, JNK-activated, insulin-resistant, first-line susceptible target cells: adipocytes, hepatocytes and myocytes. These targets can release mediators to further activate or modulate infiltrated macrophages in the target tissues. And first and second lines of cells are engaged in reciprocal activation to sustain each other in worsening the obesity-induced inflammation and insulin resistance.

On the other hand, anti-inflammatory macrophages conditioned by IL-4 and IL-13 by adipocytes can attenuate inflammation in the obese tissues (Kosteli et al. 2010. JCI. 120:3466-3479; Olefsy and Glass. 2011. Ann Rev Phy 72:219-246; Nguyen et al. 2007. JBC. 282:35279-35292; Odegaard and Chawla. 2011. Ann Rev Path Mech Dis. 6:275-297). These anti-inflammatory and pro-inflammatory macrophages are in a constant flux, and pro-inflammatory macrophages can be converted to anti-inflammatory with activation of PPARβ/δ transcription and expression the downstream anti-inflammatory genes. Myeloid deletion of PPARβ/δ also leads to glucose intolerance and insulin resistance (Oegaard et al. 2007. Nat. 447: 1116-1120). In one embodiment of the invention, galectin-3 knockdown therapy is employed for sustain a robust state of anti-inflammatory macrophages, while this therapy also convert the proinflammatory macrophages into anti-inflammatory macrophages.

In the detailed embodiment of the invention, galectin-3 knockdown increases the production of IL-10 by CD11+ dendritic cells, and macrophages, which inhibits of the inflammatory prone TNF-α production by macrophages. In addition, the galectin-3 knockdown can render macrophages across a spectrum of pro- vs anti-inflammatory phenotypes, to produce more IL-10. Thus, increase of IL-10 production by macrophages in the diseased adipose tissues via galectin-3 knockdown therapy underlies the critical amelioration of the obesity-induced inflammation, insulin resistance and T2D.

The inflammatory pathway consists of receptor activation via TNFα receptors that lead to activation of JNK via AP1, and activation of NF-κB (p50/p65 complexes) via inactivation of IKβ through IKK. The activation of AP-1 and NF-κB pathways lead to further production of TNF-α, IL-1b inflammatory molecules for causing and sustaining inflammation-induced obesity. Therefore, one embodiment of this invention of galectin-3 knockdown is to increase IL-10 production in macrophages/CD11+DC that counteract the adverse effect of TNF-α in obese tissues directly and also indirectly via attenuating the activation of AP-1 and NF-kB pathways.

Other evidences (Weigert et al. 2010. J. Clin. Endocri. 95: 1404-1411) also indicate that galectin-3 downregulation is crucial in obesity drug development. Thus (i) circulating galectin-3 was similarly elevated in T2D and obesity compared with normal weight individuals and revealed a body mass index-dependent positive correlation with leptin, resistin, IL-6, and age. In T2D patients, galectin-3 was increased in serum of patients. Moreover, since galectin-3 is required for enhancing preadipocyte proliferation from the stromovascular cells, the mass of adipose tissues can also be reduced in mass. (ii) Good cytokines such as adiponectin, produced by adipocytes downregulate obesity-induced inflammation in monocytes. Adiponectin, and the antidiabetic drug metformin both reduced galectin-3 mRNA, its cellular and soluble form, and this effect was impaired in T2D cells, strongly suggesting galectin-3 can be a target for treating obesity-induced inflammation and T2D. (iii) Heightened galectin-3 levels were accompanied with excess visceral adipose tissue from the splanchnic region and the liver to systemic galectin-3 concentrations. (iv) IL-10 is clearly relevant in obesity control. Prolonged restricted caloric intake and increased exercise led to decreased proinflammatory TNF-α, IL-6, while anti-inflammatory cytokines, adiponectin and IL-10, were significantly increased in obese subjects with metabolic risk factors.

The embodiment of this invention lays emphasis on knocking down galectin-3 expression at the level of monocyte-derived macrophages/monocyte derived DC, and in showing the knocking down monocyte-derived CD11+DC produce high levels of IL-10 expression. IL-10-producing macrophages/or dendritic cells infiltrating the adipocytes-enriched tissues (liver, skeletal muscles, adipose tissues) constitute the pivotal event of obesity-mediated inflammation (Lumeng et al. 2007. J. Clin. Invest. 117:175-184). IL-10 can serve in an auto-regulatory loop in inhibiting TNF-α, IL-6, IL-113, and NO production (Saraiva et al. 2010. Nat Rev Immunol. 10:170-181), which mediated obesity. Since IL-10 is considered one of the most important anti-inflammatory cytokine in particular in the obese tissues. Therefore, galectin-3 knockdown therapy in treating obese and T2D individuals are of critical clinical relevance and central importance. IL-10 in particular is known to inhibit TNF-α-induced activation, albeit in an NF-κB/IκB independent pathway. Thus the overall preferred embodiment of this invention is that upregulated IL-10 by galectin-3 knockdown prevents TNF-α production even from the same type of macrophage (regardless of the conventional M1 and M2 distinction). It is possible that the M1/M2 represents a convenient definition, which may not reflect the dynamic flux and functions of macrophages in the inflamed tissues.

Another preferred embodiment of this invention is to have galectin-3 knockdown in modulating the ER stress, wherein the stress comes from micronutrients and in modulating the cytokine stress wherein cytokines can cause diabetic types of inflammation.

Example 1: Galectin-3 shRNA Knocks Down Human Galectin-3 Gene Expression

RNA interference (RNAi) or gene silencing by double-stranded RNA had an immense impact on biomedical research (Fire, A et al. 1998. Nature 391: 806-811; John M. et al. 2007 Nature 449:745-747). RNAi exist in nature a fundamental gene regulation pathway in eukaryotic cells, resulting in sequence specific inhibition of gene expression. RNAi offers a potent tool to develop potential picomolar active drug candidates to appropriate targets, and can be performed through multiple double-stranded RNA forms such as micro-RNA (miRNA), short hairpin RNA (shRNA), and small interfering RNA (siRNA).

Gene knockdown with shRNA is a powerful tool for studying gene functions. Although many shRNA design programs are available, designed shRNAs should be empirically tested for their efficacies for knocking down the target gene. Initially, 10 shRNAs targeting human galectin-3 gene (LGALS3) were designed and cloned into use lentiviral vector, pLV-H1-EF1α-GFP-Bsd as reporter. HEK293 cells, expressing high levels of constitutive galectin-3 were employed. LGALS3 shRNAs and a control shRNA with non-targeting random sequences were transfected into HEK293 cells with lipofectamine 2000. Cells were harvested at days 2 or 4 after transfection. The levels of Galectin-3 protein and mRNA were measured by western blots and/or real-time RT-PCR, and results normalized with internal controls of α-tubulin and GAPDH, respectively.

Two days after transfection, galectin-3 protein levels were significantly reduced (FIGS. 1A and 1C). In shRNA 1 (SEQ ID NO:9) transfected cells, galectin-3 level was about 20% of the control. Other shRNAs, shRNA 2 to 10 (SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18), reduced galectin-3 levels more effectively than shRNA 1. shRNAs 2, 3, 8 and 10 (SEQ ID NO:10, SEQ ID NO:11, SEQ ID NO:16, and SEQ ID NO:18) down-regulated galectin-3 levels to 5-10% of the control, while shRNAs 4, 5, 6, 7, and 9 (SEQ ID NO:12, SEQ ID NO:13, SEQ ID NO:14, SEQ ID NO:15 and SEQ ID NO:17) decreased galectin-3 levels to less than 5% of the control. Four days after transfection, the overall galectin-3 protein levels were lower than control (FIGS. 1B and 1D). shRNAs 7, 8 and 9 (SEQ ID NO:15, SEQ ID NO:16, SEQ ID NO:17) reduced galectin-3 levels under 10% of the control. For shRNAs 2, 3, 4, 6, and 10 (SEQ ID NO:10, SEQ ID NO:11, SEQ ID NO:12, SEQ ID NO:14 and SEQ ID NO:18), galectin-3 levels were down to 10-30% of the control. shRNAs 1 and 5 were the least effective ones at day 4, and galectin-3 levels were about 55% of the control. For shRNAs (#11 to #18) (SEQ ID NO:19, SEQ ID NO:20, SEQ ID NO:21, SEQ ID NO:22, SEQ ID NO:23, SEQ ID NO:24, SEQ ID NO:25, SEQ ID NO:26) from Open Biosystems, galectin-3 expression was significantly reduced at day 2 after transfection (FIG. 1E), whereas there were no obvious changes of galectin-3 expression at day 4 after transfection, except for shRNA 12 (SEQ ID NO:20) (FIG. 1F).

Overall, the knockdown efficiencies are better at 2 days after transfection than at 4 days after transfection. This may be due to that shRNAs were delivered into cells by transient transfection, and most of the shRNA-containing plasmids were lost at day 4. Unlike shRNAs delivered by transfection, lentiviral vector delivered shRNA gene will integrate into host genomic DNA and express shRNA consistently. Therefore, the silencing of galectin-3 expression by lentiviral vector delivered shRNAs will be long term.

Galectin-3 mRNA levels were also measured by real-time PCR. Two days after transfection (FIG. 2A), galectin-3 mRNA levels were below 10% to that of control in HEK293 transfected with shRNAs 1, 2, 3, and 7 (SEQ ID NO:9, SEQ ID NO:10, SEQ ID NO:11, and SEQ ID NO:15). shRNAs, 3, 5, 6, 8, and 10 (SEQ ID NO:11, SEQ ID NO:13, SEQ ID NO:14, SEQ ID NO:16 and SEQ ID NO:18) down-regulated galectin-3 mRNA levels about 10-20% to that of control, while galectin-3 mRNA was reduced to 31% to that of control in shRNA 9 transfected cells. Four days after transfection (FIG. 2B), shRNAs 6, 7, 8, and 10 (SEQ ID NO:14, SEQ ID NO:15, SEQ ID NO:16, SEQ ID NO:18) kept galectin-3 mRNA levels under 50% to that of control. The lowest galectin-3 mRNA expression was detected in shRNA 7 transfected cells about 20% to that of control. Other shRNAs, i.e., shRNA 1, 2, 3, 4, 5, and 9 (SEQ ID NO:9, SEQ ID NO:10, SEQ ID NO:11, SEQ ID NO:12, SEQ ID NO:12 and SEQ ID NO:17), failed to reduce galectin-3 mRNA level below 50% to that control level. Similar to the western blot results, the lower efficiencies of shRNA at day 4 may be due to the transient transfection method.

Three steps of preparing the lenti-shRNA vector constructs are described as follows, I. Lentivirus production: $2\text{-}2.5\times10^6$ of HEK293 cells were seeded per 15 cm dish the day before transfection, incubated at 37° C. with 5% $CO_2$. Next day, cells reaching 80-90% confluence, were ready for transfection by calcium precipitation method with full change of fresh growth medium without antibiotics. For each 15-cm dish, plasmid DNAs (20 pg lentiviral plasmid, 10 pg Gag/Pol plasmid, 10 pg VSVG plasmid and 10 pg REV plasmid) were added to 0.5 ml 0.25M $CaCl_2$), and mix with 0.5 ml 2×HBS (NaCl—8 g, KCl—0.38 g $Na_2HPO_4$—0.1 g, Hepes—5 g, Glucose—1 g in 500 ml water, pH to 7.05), and incubated for 20 minutes at room temperature. Next, transfection mixture was added dropwise to the plate. 14-16 hours after transfection, the plate was changed to complete growth medium with antibiotics. 36-48 hours after transfection, viral supernatant was harvested and spun at 2000 rpm, 7 min at 4° C. in a 50 ml tube. Viral supernatant was filtered through 0.45 um filter, and the virus at this step was deemed good enough for in vitro studies. For in vivo studies, the lentivirus can be further concentrated and purified: lentivirus was made from 12-20 15-cm dishes. Virus can be concentrated by spinning with a Beckman SW28 rotor (capacity for six tubes) at 19,400 rpm. for 2 h at 20° C. Viral pellets were resuspended in 100 μl of 1×HBSS; virus can be purified through a sucrose cushion (20% sucrose in HBSS) by spinning with a Beckman SW55 swinging bucket rotor at 21,000 rpm. for 2 h at 20° C.; 13. Viral pellet, can be resuspended in 100 μl of 1×HBSS; and the lentivirus aliquoted to avoid repeating freeze-thaw cycle, and stored at −20° C. or −80° C.

II. Lentivirus Titration. A. Infective Unit: 1. Make a tenfold serial dilution of the lentivirus (from undiluted to a dilution of $10^{-6}$) in 1×PBS; 2. Seed $10^5$ HEK293 cells (500 μl) in each well of the 24-well; 3. Add 20 μl of each viral dilution to the cells, mix thoroughly but gently and incubate the cells at 37° C.; 4. Two days after infection, count GFP positive cells by FACS or fluorescent microscope (using 2-10% GFP positive cells wells to calculate lentiviral titer). This titer is infective unit/ml (IFU/ml). B. Lentivirus particle (LP): Lentivirus titer can also be calculated by the amount of p24. One ng p24 is equivalent to $1.25\times10^7$ LP. Fora typical lentivirus, 1 IFU is about 100-1000 LP. III. Lentivirus infection For efficient infection in in vitro studies, lentiviruses were used at MOI of 1 to 10. I usually use MOI of 3 or 5 for best infection. For in vivo studies, lentiviruses were used as total virus number such as $10^5$, $10^6$, $10^7$, or $10^8$ IFU, depending on the experiments.

The followings are methods for delivering siRNAs into mouse lungs (de Fougerolles. 2008.Hum Gene Ther. 19:125-132; Bitko. 2005. Nat Med 11:50; Li. 2005. Nat Med. 11:944-951) A. Intranasal administration of siRNAs into mouse lungs. BALB/c or C57BL/6 mice at the age of 6-10 weeks old are used for siRNA treatment. Mice are anesthetized with intraperitoneal injection of 0.2 ml Nembutal (5 mg/ml), and siRNAs (35-70 pg siRNAs in 100 µl) are administrated intranasally. Mice are sacrificed by cervical dislocation following anesthesia with 0.3 ml Nembutal. B. Intratracheal administration of siRNAs into mouse lungs. Female BALB/c mice at the age of 6-10 weeks old are used for siRNA treatment. siRNA (30 pg) in 100 µl RNase-free D5W (5% D-glucose in water, wt/vol) is intratracheally administered into the mouse lungs. 24 hours after siRNA delivery, mice are killed and lung tissues are harvested. siRNAs can be delivered epicutaneously to mice. Mice such as BALB/c or C57BL/6 mice, are anesthetized, shaved on back, and tape-stripped six times to removed skin barrier and integrity. A patch contains 30 to 100 µg of gal-3 siRNA in 100 µl of D5W (5% D-glucose in water, wt/vol) is placed on the shaved back. In addition, siRNA can be delivered via a cream-emulsified siRNA form (Azuma et al. 2010. Methods Mol Biol. 623:373-381.). A cream-based ointment (Johnson's baby lotion, no fragrance; Johnson&Johnson, New Brunswick, N.J.) and either dimethyl sulfoxide, or atelocollagen diluted in saline are mixed with siRNA. The siRNA-containing mixture is painted on the mouse ear skin.

The Embodiment of the Invention: We claim the composition of galectin-3 siRNA sequences, whereby these sequences are used as therapeutics for treating allergic inflammation (atopic asthma, rhinitis and dermatitis) obesity and type 2 diabetes (T2D). The present invention provides compositions and methods to silence galectin-3 expression. In one aspect, the present invention provides specific sequences that generate shRNAs and downregulate galectin-3 expression. In another aspect, the present invention provides specific sequences that generate siRNAs and silence galectin-3 expression.

In another aspect, the present invention provides the shRNA containing a stem-loop sequence, which comprises a sense sequence (19-23 nucleotides (nt) of the target sequence), a 10-nt loop sequence (UUGGAUCCAA) (SEQ ID NO:60) and an antisense sequence (19-23 nt of target antisense sequence). In another aspect, the present invention provides methods to reduce galectin-3 expression. The shRNAs are delivered into mammalian cells by non-viral or viral vectors. After transcribed, the shRNAs are directed against galectin-3 mRNA and lead to specific galectin-3 mRNA degradation. In another aspect, the invention drives transcription of the shRNA by Pol III promoters, such as human H1 or U6 promoter or mouse U6 promoter or Pol II promoters such as CMV promoter. In another aspect, the present invention uses viral vectors such as lentiviral vectors and adeno virus as the carrier of the shRNAs. In order to monitor the infected cells, the lentiviral vector contains a report gene such as green fluorescent protein (GFP). The lentiviral vector also comprises a selection marker such as Blasticidin S deaminase gene (BSD) or puromycin resistant gene to select the infected cells.

Example 2: Human Galectin-3 Knockdown Perturbs ER Stress Gene Expression

It was reported by David Ron's group that galectin-3 gene expression was drastically altered in eukaryotic cells with PERK or eIF2α gene knockdown (Harding et al. 2003. Mol Cell. 11:619-633). Therefore, we investigated whether down-regulating galectin-3 would change expression of ER stress genes in indicator HEK293 cells. All the cells were analyzed 2 days after transfection (FIG. 3A). The first ER protein we checked was BiP, an ER stress marker. Under ER stress, the expression of BiP increases dramatically. Knocking down galectin-3 up-regulated BiP expression. The largest increase occurred in cells transfected with shRNA 9 and 10. Moreover, we checked the expression of two other ER proteins, PERK and eIF2α. PERK is one of the three ER stress sensors, and eIF2α is the substrate of PERK. Down-regulating galectin-3 resulted in 2-3 fold enhancement of the total amounts of PERK and eIF2α, indicating that endogenous galectin-3 work within the PERK branch, thus galectin-3 knockdown was compensated by the increase of PERK.

Furthermore, we measured activities of folding machinery downstream of XBP1: the quantitative protein levels of protein disulfide isomerase (PDI) and endoplasmic oxidoreductin-1 (ERO1). PDI, a resident ER protein, plays a crucial role in protein folding by involving in disulfide-bond formation and isomerization. ERO1 provides oxidizing potential in ER, and mediates single electron transfer to molecular oxygen via reduction of reduced FADH2 cofactors. Knockdown of galectin-3 enhanced expression of both PDI and ERO1. In addition, we determined expression of two key quality control proteins in ER, calreticulin and calnexin. Calreticulin expression was increased in shRNA 1 and 10 transfected cells, but not in cells transfected by other shRNAs. And shRNA 6, 7, 8, 9, and 10 slightly increased calnexin expression, while shRNA 1 had minor decreasing of calnexin expression. Taken together, these results indicated that knockdown of galectin-3 altered the expression profile of crucial ER stress proteins.

Since the folding enzymes are critically dependent on the upstream XBP1, we determined whether galectin-3 knockdown enhanced XBP1 splicing in HEK 293 cells. First, we investigated XBP1 RNA splicing by RT-PCR (FIG. 4). HEK293 cells were transfected with siRNA silencing galectin-3 (Galectin-3 siRNA-4 target sense sequence: 5' UAAAGUGGAAGGCAACAUCAUUCCC-3') (SEQ ID NO:8) or scramble siRNA (Non-silencing siRNA sequence (Open Biosystem):5'-AUCUCGCUUGGGCGAG-AGUAAG-3') (SEQ ID NO:61) by Lipofectamine RNAiMAX. Cells were harvested 48 hours after transfection, and total RNAs were isolated for RT-PCR. As shown in FIG. 4, the amplified XBP1 PCR products had two forms: XBP1u and XBP1s. XBP1u is the un-spliced form that is 442 bp in size and contains a Pst I site. After Pst I digestion, the XBP1u generates two small fragments, one is about 300 bp and the other one is about 140 bp. In contrast to XBP1u, XBP1s is the spliced form and is 26 nucleotides shorter than XBP1u. Moreover, XBP1s does not contain Pst I site and is resistant to Pst I digestion. Lanes 2 to 6 were RT-PCR product of XBP1 and lanes 8 to 12 were RT-PCR product digested with Pst I. Lanes 1, 7 and 13 were the 100 bp DNA standard. DMSO treated HEK 293 cells were the control of basal level of XBP1 splicing and Tunicamycin™ (1 µg/ml) treated HEK 293 cells were the control of enhanced XBP1 splicing. Galectin-3 knock cells had 2-3 folds more spliced XBP1, XBP1s, than that of control (scramble siRNA transfected HEK 293 cells), indicating that IRE-1α was activated after galectin-3 knockdown.

Second, we measured the protein levels of XBP1s after galectin-3 knockdown by western blot. HEK 293 cells were transfected with galectin-3 siRNA-4 or scramble siRNA.

The cells without transfection were served as controls. TM at various doses (0.1, 0.5, 1.0, and 5.0 µg/ml) were added 6 hours before harvesting to enhance ER stress. Cells were harvested 48 hours after transfection. As shown in FIG. 4B, XBP1s was not detected in samples with no TM treatment (FIG. 5 lane 13 and 14) or with TM treatment at 0.1 µg/ml (FIG. 5 lane 1, 2, and 3). In HEK 293 cells treated with TM at 5 µg/ml, galectin-3 knockdown cells (FIG. 5 lane 12) had higher XBP1 expression than the cells transfected with scramble siRNA (FIG. 5 lane 11) or cells without transfection (FIG. 4B lane 10). Moreover, when cells were treated with TM at 0.5 or 1.0 µg/ml, XBP1s expression levels in cells transfected with galectin-3 siRNA (FIG. 5 lane 6 and 9) were higher than those transfected with scramble siRNA (FIG. 5 lane 5 and 8), but were lower than the un-transfected cells (FIG. 5 lane 4 and 7). Overall, XBP1s expression levels were higher in galectin-3 knockdown cells than those controls transfected with scramble siRNA. In summary, knockdown galectin-3 by siRNA increased expression of XBP1s at mRNA and protein levels.

Example 3: Protective Protein Folding and Integrated Overall ER Stress, Caused by Galectin-3

The overall impact of galectin-3 knockdown in modulating ER stress relevant in inflammatory diseases is shown in FIG. 6 (Todd et al. 2008. Nat. Immunol. 8: 663-674; Hetz and Glimcher. 2009. Mol. Cell. 35: 551-561).

Efficient Folding is Well-Managed ER Stress

The UPR is a source of stress signaling, and the chronic exposure to change of nutrient conditions such as glucose and free fatty acids, can lead to overt UPR and insulin resistance. The cellular response to ER stress, referred to as the UPR results in activation of three linked signal transduction pathways emanating from three principal ER stress sensors: IRE1α, protein kinase RNA-like endoplasmic reticulum kinase (PERK) (homologue of RNA-dependent protein kinase, PKR) and ATF6a. The combined actions of these signaling cascades serve to reduce ER stress through attenuation of protein translation to reduce the load on the ER translational machinery and through activation of transcriptional programs that ultimately serve to increase ER protein folding and maturation.

All the three arms are directly and indirectly modulated by galectin-3, culminating in attenuating JNK inflammatory responses, while elevating the XBP1 responses in counteracting insulin resistance and diabetes. XBP1 is mainly for efficient protein folding in the ER lumen, facilitated by its downstream-activated molecular chaperones, including the glucose-regulated proteins BiP and Grp94, and a variety of folding enzymes such as protein disulfide isomerase (PDI). For example, mice with genetic or diet-induced obesity show elevated ER stress, with elevated phosphorylation of PERK and IRE1α and in particular enhanced splicing of XBP1. Several markers of ER stress are also elevated in adipose tissue from obese humans. In contrast, the increase in insulin sensitivity associated with weight loss is associated with elevated XBP1 and less JNK activation. Dysfunctional UPR in the obese state contributes to insulin resistance through IRE1α-mediated c-Jun N-terminal kinase (JNK) activation, which leads to phosphorylation of insulin receptor substrate-1 (IRS-1) on inhibitory serine residues to account for insulin resistance and later a diabetic state.

Enhanced Folding Machinery by Increasing XBP1 Transcription and/or Translocation, Anti-Galectin-3 Druggable Target (i) In functional ER stress, IRE1α executes site-specific cleavage of XBP1 messenger RNA to produce a transcript (XBP1s) that encodes a potent transcriptional activator of UPR target genes to protect against inflammation. When subjected to a high-fat diet, XBP1-heterozygous mice gain more weight and become more insulin resistant than control mice. These mice also show an increase in ER stress in adipose tissue, with enhanced PERK and IRE1α phosphorylation and activation of JNK. Alterations in XBP1 can modulate insulin sensitivity. In contrast, XBP1 upregulation is causally related to diminished JNK activation and improved insulin sensitivity, indicating the importance of folding. (ii) The functional ER stress has to promote foldase implemented by transcriptional factor, XBP1, which plays critical role in preventing insulin resistance. This was confirmed from another perspective due to its role in aiding nuclear translocation of XBP1 that plays a central role in resolving the folding crisis, and prevents JNK activation, its deficiency lead to attenuate XBP1, concomitant with also a decrease in ATF6a, therefore leading to insulin resistance.

The p85α regulatory subunit of PI3K interacts with XBP1 (Winnay et al. 2010. Nat Med. 16:438-445). As a result, cells deficient in p85α or livers with selective inactivation of the gene encoding p85α show a marked reduction in ER stress and accumulation of nuclear XBP1s protein and its downstream target proteins. The physical connectivity between the regulatory subunit of PI3K and XBP1 thus further co-opts and integrates ER stress management. As an embodiment of this invention, this connection can be further enhanced by galectin-3 knockdown therapy, which provides a new therapeutic target at the interactive level of PI3K and XBP1 for treating excessive UPR-activated obesity-induced inflammation and type 2 diabetes.

Other Factors Controlling Folding:

(i) Increment of ER chaperone. ER chaperone protein oxygen-regulated protein 150 (ORP150) is induced by the UPR and plays a protective role during ER stress. Loss of ORP150 expression in either whole body or liver alone resulted in impaired glucose tolerance and decreased insulin-stimulated signaling through IRS-1. (ii) PERK pathway mutant mice (eIF2α, serine51→alanine) are equipped with non-stopped protein translation, heterozygotes become obese and develop an insulin-resistant phenotype under high fat diet, as well as an increase of body weight attributable to that observed in XBP1$^{+/-}$ mice. (iii) Yet another connection amongst PERK pathway and insulin sensitivity of target cells exists at other kinase level. The UPR-activated Trb3 protein kinase (Trb3-PK) can decrease Akt activity, and increase insulin resistance in adipocytes, while this protein kinase is upregulated by ATF-4 and CHOP through binding to its promoter. Importantly, galectin-3 and PERK/ATF-4 cooperate in anti-oxidant defense. Thus galectin-3 knockdown can intercept between PERK/ATF-4 and Trb3. The role of galectin-3 in co-opting with PERK can increase insulin sensitivity by countering Trb3-PK (Hotamisligil. 2010. Cell. 140: 900-917).

ER stress-induced inflammation can be viewed as due to inappropriate disposal of polypeptides. This lack of disposal can occur in three ways: (i) excessive protein synthesis and folding, which can be attenuated by decrease the PERK and eIF2α; (ii) lack of degradation of unfolded polypeptide, or transportation of folded proteins out of the ER lumens; (iii) lack of efficient folding due to non-concerted actions of ERO1, PDI, and chaperones. Abnormalities at the three branches for example in the presence of excess glucose can lead to ROS accumulation due to excessive folding resulting from the inappropriate disposal of polypeptides and entry/ reentry of polypeptides into the futile, inefficient folding cycle due to a lack of active XBP1.

Thus a major embodiment of the invention is toward a well-managed, integrated ER stress, centering on controlling XBP1 by galectin-3 along with its downstream folding machinery, and implicating downregulating JNK as a result. The data in Example 2 clearly showed that galectin-3 knockdown enhanced the efficient folding and resolve UPR crisis. For the crisis is resolved by simultaneously upregulating the PERK and EF2a at above a homeostatic level to reduce unfolded, de novo synthesized polypeptides, while increasing the efficiency of protein folding via ERO1/PDI pathway, and quality control and protein exit via calreticulin. The source of "excessive" protein folding is a source of inflammation, thus the burden of ER excessive stress and death of Langerhans cells in T2D may be avoided.

Therefore, one aspect of the embodiment of the invention is to alleviating the folding stress via galectin-3 knockdown therapy. In summary, galectin-3 knockdown exerts on the one hand, a direct effect on the stress response by promoting more efficient folding responses, and on the other hand, galectin-3 knockdown attenuate de novo protein synthesis by promoting the PERK branch.

As is evidenced from PERK/eIF2α knockdown studies of Ron (Harding and Ron. 2003 Mol Cell. 11: 619-633) in that galectin-3 and PERK worked in concert to relieve oxidative stress. Without new protein synthesis, there is no more entry of unfold protein without the source of oxidative stress. Henceforth enhanced protein folding, promoted by galectin-3 knockdown, shown by upregulated XBP1 and its enhanced downstream folding machinery alleviate excessive ER stress-induced inflammation as an embodiment of the invention. Thus in summary, continual UPR triggers excessive ER stress and over-stress-induced inflammation that lead to obesity and insulin resistance and T2D.

Galectin-3 plays a central role in interfering with ER over-stress by an efficient resolution of UPR crisis, which is ubiquitous in many somatic cells and organs undergoing necessary protein synthesis and lipid synthesis and other essential metabolic activities. Therefore, an overall embodiment of galectin-3 knockdown therapy resides in resolving the underlying UPR at its most fundamental levels, will alleviate undesirable excessive inflammations in multiple somatic cellular entities and multiple organs as its targets.

Example 4: Galectin-3 siRNA Inhibited Human Galectin-3 Expression in Monocyte-Derived Dendritic Cells and Macrophages Unlike vector-based shRNA, siRNA can be easily synthesized. In addition, siRNA can be improved by introduction of chemical modification and be manufactured at large scales, which make siRNA well suited as a drug. Therefore, siRNAs are the promising RNAi therapeutic for current and future preclinical and clinical studies.

SiRNAs are small double-stranded RNAs that silence genes by sequence-specific cleavage of perfectly complementary messenger RNA (mRNA). First, siRNA incorporate into a protein complex called the RNA induced silencing complex (RISC). Then, the sense strand of siRNA is cleaved. Later on, the activated RISC, which contains the antisense strand of the siRNA, selectively seeks out and degrades mRNA that is complementary to the antisense strand. After identification of potent lead siRNA candidates, the major challenge is to deliver the siRNAs to the target cells efficiently. siRNAs can be delivered with saline, liposomes, nanoparticles, or with conjugated carriers. So far, siRNAs have been successfully delivered to the central nervous system and lung epithelial cells locally and delivered to hepatocytes and tumor systemically.

siRNA is a common reagent to knockdown gene expression. The mechanism of siRNA silencing gene is the following: (i) siRNA incorporate into a protein complex called the RNA induced silencing complex (RISC); (ii) the sense strand of is cleaved; (iii) the activated RISC, which contains the antisense strand of the siRNA, selectively seeks out and degrades mRNA that is complementary to the antisense strand. As it is small and simple, siRNA is a promising drug candidate.

Furthermore, cross-species siRNA is an attractive drug candidate because the same siRNA can be used for both animal study and human clinical trials. To take the advantage of cross-species siRNAs, we designed 4 such siRNAs that target both human and mouse galectin-3 genes. The 4 cross-species siRNAs target 4 different regions of galectin-3 gene that were completely conserved in both human and mouse. siRNA: (SEQ ID NO:9, SEQ ID NO:5, SEQ ID NO:6, SEQ ID NO:7, and SEQ ID NO:8) is attractive for gene silencing. However, the big hurdle for siRNA silencing is to deliver it into target cell, especially primary cells such the one we are working on, human dendritic cells (DCs). From the literature, many groups tried to transfected human DCs, but lack of success. The best transfection efficiency we knew was about 50%. In order to transfect human DCs efficiently, we tried electroporation devices by BTX Harvard Apparatus and Invitrogen, and many transfection reagents available from market.

With comprehensive and exhaustive methods development, transfection efficiency with lipofectamine RNAiMAX to monocyte-derived DC (MoDC) can be optimized to over 85%. The optimized procedure was as follows: Lipofectamine RNAiMAX Transfection This is for 24-well plate transfection. For each well, first, prepare siRNA solution by diluting 20 pmole siRNA to 100 µl Opti-MEM I Medium without serum and Lipo solution by adding 2 µl Lipofectamine RNAiMAX to 100 µl Opti-MEM I Medium without serum. Then, mix gently the siRNA solution and the Lipo solution and incubate for 15 minutes at room temperature. Next, dilute cells in complete growth medium without antibiotics to $5 \times 10^4$-$5 \times 10^5$ cells/ml, and add 500 µl diluted cells per well. Add the siRNA-Lipofectamine RNAiMAX complexes to the cells with gentle shaking. Incubate the cells at 37° C. with 5% $CO_2$. Four hours later, add FBS to 10%. Next day, change to fresh complete growth medium with antibiotics. Cells or supernants are ready for assay 2 days after transfection.

Under the optimized transfection condition, siRNAs efficiently reduced galectin-3 gene expression in both human (MoDC) (FIG. 7A) and mouse (RAW264.7) cells (FIG. 7B). In human MoDCs, cells transfected with non-targeting siRNA had similar galectin-3 level as the cells without transfection, whereas galectin-3 siRNAs reduced galectin-3 expression at various levels. Galectin-3 siRNA-1 (SEQ ID NO:5) and siRNA-2 (SEQ ID NO:6) slightly decreased galectin-3 expression (50% of the control level), while galectin-3 siRNA-3 and -4 (SEQ ID NO:7, and SEQ ID NO:4) reduced galectin-3 expression significantly (over 90% reduction). Galectin-3 siRNA-4 (SEQ ID NO:8) is the most potent inhibitor of galectin-3 expression in human MoDCs. For mouse macrophage cell line, RAW 264.7, comparing with non-targeting siRNA control, galectin-3 expression levels decreased about 50% in cells transfected with galectin-3 siRNA-1, 2, and 3 (SEQ ID NO:5, SEQ ID NO:6, and SEQ ID NO:7) and over 90% in cells transfected by galectin-3 siRNA-4 (SEQ ID NO:8). In summary, siRNA-3 and 4 (SEQ ID NO:7, and SEQ ID NO:8) are potent inhibitors of galectin-3 expression in MoDC, while siRNA-4 (SEQ ID NO:8) is the best inhibitor of galectin-3 expression in mouse RAW264.7 cells. siRNA-1 and 2 (SEQ ID NO:5, and SEQ ID NO:6) had the least effect on galectin-3 expression in both human and mouse cells.

Example 5: Knocking Down Galectin-3 Expression in MoDCs in Regulating Cytokine Expression Monocyte-derived dendritic cells (MoDC) were prepared from normal human blood donors, and cultured via two stages in GM-CSF/IL-4, followed by 24 hr incubation in maturation cocktails. CD83 is a common marker for mature human blood DC. Another DC marker is CD205, which is an endocytic dendritic receptor that mediates efficient processing and presentation of antigens on MHC class II productions. CD205 is highly expressed by DCs, particularly on $CD8^+$ DCs. In order to distinguish DCs from other cells, we labeled DCs with APC-anti-human CD83 antibody and PE-anti-human CD205 antibody, then analyzed the cells by FACS (FIG. 8A). Both APC-CD83 positive cells and PE-CD205 positive cells were about 51% (FIG. 8A). In addition, we determined intracellular proteins such as IL-12 (p35) and OX40L, by FACS analysis. IL-12 (p35) was labeled p35 by APC-anti-human p35 antibody and PE-anti-human OX40L antibody. There were about 74.8% p35 positive cells (FIG. 8B). The results demonstrated that we have enablement platform to accurately quantify DCs and cytokines produced by DCs.

These MoDC were characterized according to two surface DC markers into about 58% CD83+, CD205+ double positive cells along with ~10% CD205 single positive cells (FIG. 8A). Next, intracellular staining of IL-12 and OX40L were conducted. FIG. 8B showed that the majority of these DC~75% constitutively expressed IL-12 and close to 50% of MoDC co-expressed intracellular OX40L.

Knockdown galectin-3 in MoDCs was also confirmed by flow cytometry (FIG. 8C). MoDCs were transfected with siRNA-4 and the cellular galectin-3 levels were detected by staining with FITC-anti-human galectin-3 antibody. The siRNA transfected MoDCs had significant lower galectin-3 (lower fluorescent intensity) than those in control MoDCs. After siRNA knockdown, the galectin-3 positive MoDCs were down to 34.8%. The results confirmed that siRNAs can significantly reduce galectin-3 expression in MoDCs.

One of the signals that dendritic cells (DCs) activate T lymphocytes is to release a number of soluble and membrane-bound ligands. Interleukin (IL)-12 is one of the well-studied signal agents produced by DCs. IL-12 polarizes Th cells toward Th1 phenotype and is an attractive candidate to switch allergy-induced Th2 phenotype. Moreover, DCs can be activated by toll-like receptors (TLRs) that sense microbial products and initiate adaptive immune response. Lipopolysaccharide (LPS) triggers TLR4, while imiquimod and R848 trigger TLR7/8. IFN-γ is well known for its function to enhance IL-12 expression. To study the expression of cytokine expression after stimulation, MoDCs were treated with various stimuli such as imiquimod, R848, LPS, and IFN-γ. Imiquimod (1, 5, and 10 pg), R848 (1, 5, and 10 pg), or Imiquimod+R848 (1, 5, and 10 pg) had no significant increase of IL-12 expression (FIG. 9A), but slightly enhance 11-23 expression (FIG. 9B). LPS (*E. coli* 026:B6, *E. coli* 0111:B4, and *E. coli* 00157:H7) treatments at 50 ng/ml or 1 μg/ml increased IL-12 expression 7 to 10 folds and IL-23 expression 3-6 folds. IFN-γ (at 100 and 1000 U/ml) up-regulated IL-12 levels 10 folds and IL-23 levels 24 folds. Combined IFN-γ and LPS had the most increasing for both IL-12 (from 19 to 130 folds) and IL-23 (from 7 to 55 folds). Combination of LPS with imiquimod or R848 also significantly increased IL-12 expression. Therefore, these results provided a guideline for the using of stimuli and their doses to induce IL-12 expression from MoDCs.

Moreover, galectin-3 siRNA knockdown significantly reduced in MoDC stimulated with innate TLR ligands (FIG. 9C). Galectin-3 siRNA knockdown in MoDCs was described in example 3. A non-targeting siRNA was used as control. MoDCs were harvested 48 hours after siRNA transfection, total RNAs were isolated and used for cDNA synthesis. LGALS3 mRNA levels were quantified by real-time PCR. Actin was used as an internal control. LGALS3 mRNAs levels in galectin-3 knockdown cells were down 70% (no treatment and LPS) or 80% (R848 or R848/LPS) of the un-treated cells transfected with scramble siRNA control. CK is a non-silencing siRNA that does not target any human or mouse genes, and is used as control.

Example 6: Secretion of Cytokines (IL-12, IL-23, and IL-10) after Galectin-3 Knockdown The embodiment of galectin-3 siRNA knockdown in controlling multiple cytokines expression in inflammatory diseases is illustrated (FIG. 10). Although IL-12 was produced more in galectin-3 deficient mice, there is no knowledge whether in a real-life situation in humans phenotypic knockdown at the message levels, where there is no galectin-3 deficiency to start with, will yield predictive outcome. Moreover, genetic deficiency does not provide a therapeutic modality except offering a state of the affair of a static nature. Gene therapy, on the other hand, offers a direct proof and enablement of the druggable sites, which has no precedents. Thus the phenotype re-created from a knocking down of an active gene amongst a complete set of competent genes, galectin-3 included, is different from a genetic disease with a procreated deficiency.

We showed herein that knockdowns galectin-3 in DCs enhance IL-12 expression, an indication of Th1 polarization. Since IL-10 and TGF-β are well known anti-inflammatory cytokines, we are interested in measure the secretion of IL-10 and TGF-β too. To investigate the effects of galectin-3 knockdown in DCs, we monitor the changes of cytokine (IL-12, IL-23, IL-10, or TGF-β) levels after down-regulation of galectin-3 in MoDCs with/without stimulation. Galectin-3 expression levels in MoDCs were down-regulated by siRNAs (galectin-3 siRNA-3, and 4) and the cytokine (IL-12, IL-23, IL-10, or TGF-β) levels in supernatants were measured by ELISA assays. IL-12 levels (FIG. 11A) were significantly higher in galectin-3 knockdown MoDCs than those in control MoDCs treated with scrambled siRNA as control, especially in cells treated with R848, LPS, IFN-γ+LPS, Imiquimod+LPS. IL-12 expression was greatly stimulated by R848+LPS in both control and galectin-3 knockdown MoDCs. No significant differences on IL-12 levels were noticed among control and this particular group of galectin-3 knockdown MoDCs, presumably due to the supra-optimal stimulation that saturated the IL-12 expression.

The changes on IL-23 expression levels (FIG. 11B) between control and galectin-3 knockdown MoDCs were different from IL-12 expression. Comparing with control MoDCs, galectin-3 knockdown cells treated with R848 or R848+LPS had obvious decreasing of IL-23 levels.

Moreover, galectin-3 knockdown MoDCs had significant higher levels of IL-10 production (FIG. 11C) from all treated and un-treated cells than those from control MoDCs. There were no significant change of TGF-β expression between MoDC control and knockdown MoDC (FIG. 11D). The results demonstrated that down-regulation of galectin-3 in MoDCs increased IL-12 and IL-10 expression, inhibited the IL-23 expression, and no effect on TGF-β expression. Therefore, siRNAs that down-regulate galectin-3 expression and increase IL-12 and IL-10 expression in DCs are good drug candidates to regulate Th2 responses and allergic responses.

In addition to determine cytokine protein levels by ELISA, we also measured the mRNA levels of cytokines in galectin-3 knockdown MoDCs and with/without IL-12 suppression/stimulation. Thymic stromal lymphopoietin (TSLP) potently transduced a unique Th2-inducing signal in DCs and suppresses IL-12 expression. On the other hand, treatment with LPS, R848/LPS, and IFN-γ/LPS will stimulate IL-12 expression. In order to measure the specific mRNA levels of cytokine (IL-12 or IL-23), we determined the mRNA levels of IL-12 specific subunit (p35) and IL-23 specific subunit (p19). The mRNA levels of p35 (IL-12) in galectin-3 knockdown MoDCs were higher than those in the control MoDCs (FIG. 12A). The mRNA levels of p19 (IL-23) in knockdown MoDCs (no treatment, treated with TSLP or LPS) were lower than those in control MoDCs (FIG. 12B). The results indicated that galectin-3 knockdown MoDCs had higher IL-12 (p35) transcription levels and lower IL-23 (p19) transcription levels than the control cells.

Example 7: Micronutrient-Induced, ER Stressors and the 'Four' Arms of ER Stress

ER stress and nutrients (Hummasti and Hotamisligil. Cir Res. 107: 579-591; Gregor and Hotamisligil. 2011. Ann Rev Immu. 29: 415-445): ER handles stress and more importantly coordinate metabolic responses through its ability to control the synthetic and catabolic pathways of also various micronutrients. Three branches of ER stress can be differentially activated due to various levels of micronutrient exposure, obesity-induced inflammation, and galectin-3 levels can regulate ER stress levels. (i) The UPR may be induced by the increased demand for protein synthesis under nutrient excess and expansion; and the excess nutrients themselves may serve as initiating signals inducing ER stress. In the case of glucose, notably, two major heat-shock proteins, BiP and Grp 94, both glucose-sensitive chaperones are upregulated. Homeostatic ER stress is maintained by ATP generated by glucose metabolism, and BiP and Grp94 hydrolyzing ATP during active protein synthesis and folding, and the dissociation of the three branches of upstream of ER stress to release PERK, IRE1α and ATF6 to account for the unfold protein responses (UPR).

Thus all three canonical UPR branches are engaged with glucose metabolism. Over-glucose supplies create pathological ER stress, over-burden of secretion of insulin, and insulin resistance of multiple cell types. (ii) Indeed, paradoxically, the cause of ER stress in obesity is glucose deprivation, a known condition of UPR activation in many cell types, including adipocytes. Glucose deprivation occurs as a result of cellular insulin resistance, i.e., the starvation of the adipose in the face of plenty. (iii) Notably, serum free fatty acid (FFA) levels are increased in obesity, and studies have shown that FFAs can induce the UPR in hepatocytes, cardiomyoblasts, pancreatic β-cells, and macrophages via TLR4 receptor, and levels of stress level can be potentiated by hypoxia. Hypoxia, typically prevalent in obese adipose tissue (Hosogai et al. 2007. Diabetes. 56: 901-911), thus provides a link to ER stress contributing to JNK activation and causing insulin resistance of adipocytes.

Despite the origin of ER stress, an embodiment of the invention is that galectin-3 knockdown, cooperating with the PERK branch, can counteract levels of ROS level due to FFA signaling in the presence of hypoxia in these obese tissues, and in so doing, can improve insulin receptor signaling. (iv) Although ER stress trigger inflammation in one direction; reciprocally Inflammation can in turn induces the UPR. Indeed, TNF-α action was shown to activate the UPR. The mechanism of TNF-α UPR induction was shown to be dependent upon ROS; it follows that oxidative stress is an obesity-related ER stress as evidenced by an increase in oxidative stress markers in the adipose tissue of obese/insulin-resistant mice and humans.

Thus in this connection, galectin-3 knockdown as an embodiment in modulating the altered endogenous state of redox, can influence over obesity-induced inflammation and insulin resistance. (v) ER stress at the CNS levels relating over-nutrition of micronutrients to energy imbalance and obesity. Neuropeptide-secreting hypothalamus is the headquarter for regulating energy homeostasis, linking nutrient to energy imbalance and obesity. Leptin and insulin resistance develop in these neurons in nutrient excess, mediated by PI3K, and mTOR and IKKβ/NF-κB activation in obesity and T2D. Therefore, in one embodiment of the invention, galectin-3 knockdown therapy may attenuate neuronal PI3K, mTOR and IKKβ/NF-κB IKKβ in the hypothalamus of the CNS for over-nutrition induced T2D.

In addition, ER can also propagate ER stress-related signal from the lipid components. (i) ER is a major site of triglyceride (TG) droplet formation. In response to fatty acid accumulation within the cell, TG droplet formation occurs as an energy storage and lipid-neutralizing mechanism. The adipocyte stores TG and cholesterol in the droplet form, and release of fatty acids from TG storage by lipolysis can trigger macrophage activation via the afore-mentioned free fatty acid and TLR4 pathway, and obesity-related inflammation. (ii) ER's role in cholesterol and lipid sensing. Cellular levels of cholesterol are regulated through the sterol-regulatory element binding protein (SREBP) family of transcription factors. In response to insulin signaling, SREBP1c is released from ER, entry into the Golgi and finally translocated to nucleus to upregulate lipid synthesis in harmony with cholesterol synthesis controlled by the two other isoforms (-1a, -2) under normal circumstances. Under overt ER stress due to lipid overload, insulin resistance is developed and SREBP1c is downregulated for lack of release via ER, and the homeostasis of cholesterol and lipid synthesis is profoundly affected in obesity-induced inflamed adipocytes. Therefore, one embodiment of the galectin-3 knockdown is to alleviate insulin resistance of adipocytes by blunting inflammatory signaling during overt lipid loading that desensitizes release and utilization of SREBP-1c, and consequently leading to dysfunctional lipid/cholesterol homeostasis.

Moreover, the nutrient-responsive mammalian target of rapamycin (mTOR) pathway upregulates protein synthesis that naturally increases protein translation and folding in the ER. Nutrient overload could engage this pathway and leads to a translational demand overwhelming the ER as mTOR activity is increased in obesity and insulin resistance. Thus obesity-related increase in mTOR activity contributes to an ER stress response. The ER is exquisitely sensitive to glucose availability, its deprivation, or the excess is perceived by the ER via its stress pathways and lead to the mounting of its adaptive responses as an UPR.

Finally, there is yet another arm of the ER stress in store concerning a unique role for the eIF2α kinase PKR in linking lipid sensing to ER stress-induced inflammation and metabolism. PKR is markedly activated by lipids and during obesity plays a critical role in the activation of JNK and the inflammatory response. PKR also directly interferes with insulin action by interacting with IRS1. Thus, PKR therefore integrates insulin action, pathogen responses, and translational control with nutrient sensing and ER stress. And this PRK may be called the fourth arm of ER stress, along with nutrients and ER stress account for integrating JNK, IKK. The reduced phosphorylation of PKR may be affected by galectin-3 knockdown in improving insulin resistance.

Example 8: Macrophages as the Sustaining Inflammatory Cells for Obesity-Induced Inflammation and Insulin Resistance, and Embodiment of Galectin-3 Knockdown in Upregulating IL-10 to Dampening Inflammation Fine-Tuning and Silencing Obesity-Induced Pro-Inflammatory Macrophages by Galectin-3 Knockdown.

In this diagram, (Kosteli et al. 2010. JCI. 120:3466-3479; Odegaard et al. 2007. Nat. 447: 1116-1120; Olefsy and Glass. 2011. Ann Rev Phy 72:219-246; Sell et al. 2008: 294: E1070-E1077; Hajer et al. Eur. Heart J. 29: 2959-2971; Nguyen et al. 2007. JBC. 282:35279-35292; Odegaard and Chawla. 2011. Ann Rev Path Mech Dis. 6:275-297), we show the galectin-3 knockdown can upregulate IL-10 to inhibit the downstream pathways of TNF-α in adipocytes and macrophages. Adipocytes normally condition Th2 cytokines to promote anti-inflammatory macrophages These macrophages in turn secret IL-10 to recondition T2 cytokine producing adipocytes on the one hand; IL-10 also play a central role in the staying power of anti-inflammatory macrophages on the other hand, thereby a transformation of anti-inflammatory macrophages to TNF-α producing macrophages is blunted. We do not favor the paradigm of M2 and M1, since phenotypes of macrophages are flexible and there is a constant flux of cellular activities.

During obesity-induced inflammation, adipocytes and proinflammatory macrophages can both produce TNF-α to perpetuate and expand the adipocytes in obese tissues and sustaining TNF-α-activated proinflammatory macrophages. Therefore, a major embodiment of galectin-3 knockdown therapy plays a critical role in rendering anti-inflammatory macrophages to stay put, while converting proinflammatory macrophages into anti-inflammatory state; furthermore galectin-3 knockdown blunts the two-way cross talks amongst proinflammatory macrophages with inflamed adipocytes via TNF-α signaling. Thus galectin-3 knockdown therapy produces a maximal treatment effect in profoundly reducing obesity-induced inflammation, improving insulin sensitivity in overcoming insulin resistance, and ameliorating T2D.

On Paradoxical Effect of Targeting PPARγ:

The two opposing actions based on PPARγ targeting (Odegaard et al. 2007. Nat. 447: 1116-1120; Olefsy and Glass. 2011. Ann Rev Phy 72:219-246; Odegaard and Chawla. 2011. Ann Rev Path Mech Dis. 6:275-297). The peroxisome proliferator-activated receptor γ (PPARγ) as a member of the nuclear receptor superfamily is regulated by free fatty acids (FFAs), required for adipocyte differentiation. In this perspective, T2D drug dampening over-expression of PPARγ has been development. PPARγ however also expressed in macrophages, and indeed to the benefit of the body mass in that it downregulates a host of proinflammatory gene pathways. Therefore, deletion of macrophage PPARγ in PPARγ KO mice lead to heightened inflammatory pathway activation, glucose intolerance, and insulin resistance on even normal diets. The drug treatment at different tissue levels can lead to desirable vs undesirable effect. Therefore in our view PPARγ appears a complex drug target for improving insulin resistance because its upregulated levels soothing inflammation at level of adipocytes at the expense of increasing proinflammatory macrophages. In this vein, the embodiment of galectin-3 knockdown presents a different approach than that of dampening PPARγ.

Description of the Central Macrophage Lesions

In this diagram, we showed two opposing actions of macrophages (Kosteli et al. 2010. JCI. 120:3466-3479; Olefsy and Glass. 2011. Ann Rev Phy. 72:219-246; Sell et al. 2008: 294: E1070-E1077; Nguyen et al. 2007. JBC. 282: 35279-35292; Odegaard and Chawla. 2011. Ann Rev Path Mech Dis. 6:275-297). Macrophages are recruited to adipose tissue upon high-fat feeding. These proinflammatory macrophages engulfing Tg, assume appearance of foam cells. FFA binding to TLR4 receptors can render proinflammatory macrophages, expressing TNF-α, 116 and Nos2, F4/80+ CD11c+ (a bona fide DC marker), clustered as the crown-like structure around the central adipocytes, causing cell death. Proinflammatory macrophages expressed low levels or lack IL-10 secretion, but high levels in secreting TNF-α, and cause inflammation and insulin resistance in target cells, hepatocytes, myocytes, and adipocytes. In contrast, macrophages from lean mice expressed IL-10 and Ym1, arginase 1. The anti-inflammatory cytokine IL-10 protected adipocytes and other targets from TNF-α-induced insulin resistance. IL-10 anti-inflammatory effect on targets: (i) STAT3 phosphorylation by the IL-10 receptor has been shown to be required for its anti-inflammatory effects. Treatment of adipocytes with IL-10 leads to the rapid tyrosine phosphorylation of STAT3, and activates Akt and PI3K pathways via insulin receptor substrate (IRS) proteins to enhance insulin sensitivity. (ii) IL-10 exerts anti-inflammatory effects in macrophages themselves and other cells, antagonizing TNF-α action, which activates glucose transporter 4 (GLUT4) among other TNF-α downstream events. (iii) IL-10 inhibits secretion of the chemokine MCP-1 in states of obesity.

Galectin-3 is expressed abundantly in macrophages regardless of the state of pro-vs anti-inflammation. Thus galectin-3 knockdown can ubiquitously render macrophages of a wide spectrum of all activation and/or differentiation states, to initiate IL-10 production and/or produce large quantity of IL-10. Therefore a preferred embodiment of this invention is to cause high levels of IL-10 production by both proinflammatory and anti-inflammatory macrophages in the obese tissues. In another preferred embodiment, the inflammatory macrophages are converted on the entire phenotypic features to the anti-inflammatory macrophages. Another embodiment of the invention is upregulate both IL-10 and XBP1 concomitantly in pro- and anti-inflammatory macrophages. Another preferred embodiment of galectin-3 knockdown is to modulate both the ER stress-induced inflammation as well as cytokine-induced inflammation caused by diverse micronutrients, including high fat diet, whenever the signal transduction of the micronutrient alone or in combination causes diabetic types of inflammation.

Example 9: Protection of Oxidative Stress of UPR by Galectin-3 Knockdown

Galectin-3 can act in concert with PERK in antioxidant defense, and galectin-3 is upwardly compensated in PERK and ATF4 knockdown mice (Harding et al. 2003. Mol Cell. 11:619-633). Thus by influencing PERK, galectin-3 is implicated in the regulating the glucose mechanisms in pancreas. Excessive insulin synthesis to overcome insulin resistance at the insulin receptor signaling levels causes the synthetic ER stress and death of β-Langerhans cells. The synthetic ER stress is managed by PERK, involving in the survival and function of pancreatic islet cells. The disturbed glucose metabolism noted in PERK-deficient mice as well as in eIF2α mutant mice, has been linked with islet cell dysfunction or death triggered by overt ER stress. Thus, galectin-3 implicated for compensating for PERK deficiency may be required for survival of β-Langerhans cells by providing anti-oxidant defense in elevating NRF2; alternatively the ATF-4 mediated reduced environment is not efficient for protein folding, therefore enhancing the folding efficiency by galectin-3 knockdown prevents repeated entry of unfolded protein into the futile folding cycles, resulting in heightened levels of ROS. Thus galectin-3 is bifunctional in that transiently knocking it down can augment protein folding, while restoring its activity then assists PERK to reduce oxidative stress in the ER lumens.

The bifunctional protection of galectin-3 to ease ER stress is applicable to hepatocytes in the liver in a disease model, wherein eIF-2a is knocked down by constitutively active Gadd34 in the liver. Thus there is a constant lack of reducing environment for the liver, in that unresolved UPR due to rounds of futile folding leads to high levels of oxidative stress, while there is management in place to render a reduced microenvironment to attenuate or counter the oxidative stress damage. In this scenario, galectin-3 will be upregulated to compensate for the lack of phosphorylated eIF2α, which activates ATF-4-mediated antioxidant defense. Although seemingly paradoxical, too much reduced state of protein, i.e., unfolded protein, indeed contributes to dysfunctional ER stress due to unresolved UPR that reflects an insufficiency of folding machinery, which fails to reach the overall necessary quota of folded protein. In this condition, the attenuation of galectin-3 due to galectin-3 knockdown is relevant and fundamentally important in causing more efficient folding machinery in order to resolve the UPR crisis. The fine toning of integrated ER stress is thus brought about by galectin-3 knockdown because it augments the folding by upregulating XBP1, while it causes PERK upregulation shown in Example 3 to 6, to compensate for the loss of antioxidant defense.

Henceforth, the balance of the biphasic toning by galectin-3 knockdown can resolve any insufficiency caused by a dysfunctional eIF2α. Failure to remove the unfolded protein: a lack of a disposal function due to insufficient ERAD and XBP1 coupled to sustained de novo protein synthesis, will eventually activate the full fledged IRE-1α (IRE-1αsome)-dependent activation of JNK (Hetz and Glimcher. 2009. Mol Cell. 35: 551-561), which as an effector enzyme causes insulin resistance, and prevents blood glucose release from hepatocytes during fasting in that gluconeogeneis also becomes defective during prolonged ER stress by overstressing the three branches.

Therefore an embodiment of the invention underlies this bifunctional alternate phasing or a combined action of galectin-3 knockdown that prevents or delays high glucose-mediated β-Langerhans cell death. Similar dual pro-folding machinery coupled to antioxidant defense pathway may operate in glucose metabolism in hepatocytes, myocytes and lipid sensing in adipocytes in that the embodiment of galectin-3 knockdown achieves embodiment of dual protection via an integrated XBP1 coupled to PERK/eIF2α branch of ER stress management.

Of note, one of the main injuries of uncontrolled UPR resides in excessive production of superoxide anions resulting in dangerous levels of oxidative stress. This is due to a futile protein folding cycle of unfolded proteins and continual recycling without protein exit from the ER lumens; alternatively high ROS levels are due to high folding output of a given protein species such as insulin synthesis in the β-Langerhans cells or immunoglobulins in the plasma cells. ROS accumulation is due to the enzymes responsible for forming disulfide bonds via ERO1p and ERV2p, coupled with PDI that catalyzes the unfolded polypeptides as substrates. Next, the one electron was transferred from the FADH2 center of ERO1 to molecular oxygen in order to regain the oxidizing currency by oxidizing the reduced PDI for other unfolded protein via a generative redox folding chain.

This folding process requires unfolded protein substrates presented by BiP at the expense of ATP hydrolysis. This may in part explain the base of glucose-stimulated UPR and ER stress. Notably, this single electron-reduced molecular oxygen, i.e., superoxides, accumulates during increased protein folding due to UPR activation and is toxic to cells. Therefore, the embodiment of the invention of galectin-3 knockdown promotes XBP-1 and its downstream folding machinery can expediently remove the very source of ER stress, i.e., oxidative stress owing to ROS. Galectin-3 knockdown therefore can prevent IRE-1α to undergo overt stimulation leading to activation of JNK and IKKI3 and downstream inflammation events.

The UPR has evolved to anticipate this increase in ROS especially during ER stress via PERK-mediated activation of an antioxidant program through the transcription factor Nrf2 to neutralize toxic species. Despite these built-in protective measures, prolonged UPR activation still results in increased ROS levels that may elicit inflammatory responses, thereby providing yet another potential link between ER stress and inflammation. In this vein, galectin-3 plays a key function in cooperating with PERK, eIF2α, and Nrf2 in ensuring the reductive environment (at the cost of efficient folding). Therefore the balance of integrated (ER) stress management hangs in the balance between decreased entries of newly synthesized species (obviating oxidative folding) vs efficient folding (to reduce folding intermediates).

Downstream ATF-4 and Nrf2 can play a key role in compensating for galectin-3 knockdown in order to achieve this balanced, manageable/integrated ER stress. Therefore one embodiment of the invention of galectin-3 knockdown resides in the upregulation of effector Nrf2, which upregulates phase 2 enzymes and endogenous glutathione. It is important to point out that the reduction of JNK activation relies on the elevated XBP1 activities, which takes care of crisis folding, critically reduced level of insulin resistances in balance with upregulated Nrf2, its downstream phase 2 enzymes and increased glutathione levels in the ER lumens.

ER Stress Mediated by ROS Via Innate Receptor TLR4.

Innate Toll-like receptor (TLR) and IRE1-XBP1 pathways are interconnected and act in concert to maximize innate immune responses to pathogens. XBP1 mRNA was matured to its active form by TLR4 and TLR2 via a mechanism that required the NADPH oxidase NOX2 with TRAF6 (Martinon et al. 2010. Nat Immunol. 11: 411-418). TLR activation of XBP1 requires ROS dictated by NOX2. Other cytokine-mediated signal transduction pathways have been shown to trigger this aspect of the ER-stress response in a ROS-dependent manner. TNF-α treatment promotes the activation of PERK, ATF6a and IRE1 in a ROS-dependent manner; in contrast ROS production by arsenite activates the phosphorylation of eIF2α but not of PERK or IRE1α, which indicates that different oxidative stresses selectively activate different downstream pathways.

Another embodiment of the invention of galectin-3 knockdown treatment can lead to reduced ROS due to overcompensation of Nrf-2. Soluble galectin-3 induces ROS in neutrophils. Therefore another preferred embodiment of galectin-3 knockdown resides in abrogation of the auto-regulatory enhancing loop due to interaction of soluble galectin-3 and its surface glycans on macrophages or DC, leading to accumulating ROS.

The embodiment of this invention resides in rendering the pro-folding function more efficiently by elevating the transcription factor, XBP1, accompanied by less oxidative stress. Galectin-3 knockdown upregulates the XBP1 levels therefore is indicated as a suitable candidate for correcting insulin resistance. Also, the relationship between ER stress and oxidative stress is not one-sided as ROS generated through a third party inflammation or ROS generated at the expense or at level of another organelle, i.e., dysfunctional mitochondria could also lead to accelerated ER dysfunction.

Interestingly, TLR4 and TLR2 stimulation triggered phosphorylation of IRE1a and maturation of XBP1 mRNA in macrophages in the absence of other ER-stress markers, such as processing of ATF6a, phosphorylation of PERK or induction of ER stress-dependent genes encoding CHOP, BiP, ERdj4 and PDI (Todd et al. 2008. Nat Immunol. 8: 663-674). Therefore another embodiment of the invention resides in modulation of ER stress induced by interactions of pattern recognition danger signal and the innate TLR on DC and macrophages; moreover, the embodiment of galectin-3 knockdown can activate XBP1 via a folding-independent vs folding dependent pathway to alleviate inflammatory responses.

---

I claim:

1. A small interfering RNA (siRNA) targeting human galectin-3 to treat allergic inflammation, wherein said siRNA comprises a sense strand of 19-25 nucleotides in length and an antisense strand of 19-25 nucleotides in length, wherein the sense strand comprises a sequence selected from the group consisting of SEQ ID NO: 4, SEQ ID NO: 16, SEQ ID NO: 17, and wherein, respectively the antisense strand comprises a sequence selected from the group consisting of SEQ ID NO: 8, SEQ ID NO: 34, SEQ ID NO: 35, and wherein the double-stranded siRNA can be introduced to a cell and suppresses human galectin-3 gene expression in said cell, whereby allergicinflammation, asthma, obesity inflammation, insulin resistance, and type II diabetes are alleviated.

2. A composition comprising the siRNA of claim 1 and a pharmacological carrier.

3. The siRNA of claim 1, wherein each of the sense strand and the antisense strand comprise at least one chemically modified nucleotide base.

* * * * *